United States Patent
Takasu et al.

(10) Patent No.: US 8,101,759 B2
(45) Date of Patent: Jan. 24, 2012

(54) ACENAPHTHOPYRIDINE DERIVATIVE, MATERIAL OF LIGHT-EMITTING ELEMENT, LIGHT-EMITTING ELEMENT, LIGHT-EMITTING DEVICE, AND ELECTRONIC APPLIANCE

(75) Inventors: Takako Takasu, Leuven (BE); Ryoji Nomura, Kanagawa (JP); Satoko Shitagaki, Kanagawa (JP); Satoshi Seo, Kanagawa (JP)

(73) Assignee: Semiconductor Energy laboratory Co., Ltd. (JP)

( * ) Notice: Subject to any disclaimer, the term of this patent is extended or adjusted under 35 U.S.C. 154(b) by 340 days.

(21) Appl. No.: 12/409,695

(22) Filed: Mar. 24, 2009

(65) Prior Publication Data

US 2009/0247753 A1    Oct. 1, 2009

(30) Foreign Application Priority Data

Mar. 28, 2008 (JP) ................. 2008-086574

(51) Int. Cl.
*C07D 401/04* (2006.01)
*H01L 51/50* (2006.01)
(52) U.S. Cl. .......................... 546/75; 313/504
(58) Field of Classification Search ............. 546/75; 313/504
See application file for complete search history.

(56) References Cited

U.S. PATENT DOCUMENTS

2009/0243476 A1  10/2009 Nomura et al.

FOREIGN PATENT DOCUMENTS

| JP | 10-340784 | 12/1998 |
|----|-----------|---------|
| JP | 2006-16363 | 1/2006 |
| JP | 2006-241053 | 9/2006 |

OTHER PUBLICATIONS

International Search Report re application No. PCT/JP2009/056422, dated May 19, 2009.
Written Opinion re application No. PCT/JP2009/056422, dated May 19, 2009.
Tao, Y.T. et al, "Sharp Green Electroluminescence from 1 H-pyrazolo[3,4-b] Quinoline-Based Light-Emitting Diodes," Applied Physics Letters, vol. 77, No. 11, Sep. 11, 2000, pp. 1575-1577.

*Primary Examiner* — Charanjit Aulakh
(74) *Attorney, Agent, or Firm* — Husch Blackwell LLP

(57) ABSTRACT

It is an object to provide a new compound which is suitable for a material of an electron-transporting layer of a light-emitting element. In particular, it is an object to provide a compound which can be used for forming a light-emitting element capable of emitting light at a low drive voltage. An acenaphthopyridine derivative represented by the following general formula (G1) is provided. In the formula, Het represents a pyridyl group or a quinolyl group.

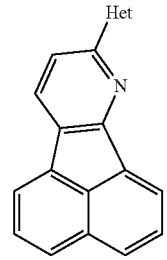

(G1)

10 Claims, 11 Drawing Sheets

ACENAPHTHOPYRIDINE DERIVATIVE, MATERIAL OF LIGHT-EMITTING ELEMENT, LIGHT-EMITTING ELEMENT, LIGHT-EMITTING DEVICE, AND ELECTRONIC APPLIANCE

TECHNICAL FIELD

The present invention relates to a new acenaphthopyridine derivative. The present invention also relates to a material of a light-emitting element, a light-emitting element, a light-emitting device, and an electronic appliance which use the acenaphthopyridine derivative.

BACKGROUND ART

Organic EL televisions are being acknowledged by the general public as next generation displays after plasma televisions and liquid crystal televisions. In organic EL televisions, a light-emitting element in which a layer including an organic compound is interposed between electrodes and light is emitted by supplying a current (hereinafter referred to as a light-emitting element) is used for a pixel. Therefore, extra space or a backlight is not needed, and very thin displays can be obtained. In addition, organic EL televisions have high visibility and high response speed, and furthermore, can easily achieve a high contrast ratio. Accordingly, organic EL televisions are undoubtedly next generation displays which can display high-quality images.

However, organic EL televisions which are now on the market consume approximately 1.5 times more power than liquid crystal televisions in the same size. Organic EL televisions have the potential to achieve lower power consumption than that of liquid crystal televisions, but they have not yet been developed to that level.

These days, it is required to use fewer resources and less energy. Thus, if organic EL televisions achieve lower power consumption than that of liquid crystal televisions, the organic EL televisions can be very attractive products which can improve the quality of life and conform to environmental awareness at the same time, so a demand for lower power consumption is high.

There are many approaches to achieving lower power consumption of displays. Reduction in drive voltage of a light-emitting element itself is a very simple and effective approach. In particular, the drive voltage of a light-emitting element greatly depends on a material which is used. Hence, a material which can reduce the drive voltage of a light-emitting element is being developed.

In many cases, a light-emitting element is formed using plural layers having different functions. Typically, a layered structure in which a hole-injecting layer, a hole-transporting layer, a light-emitting layer, an electron-transporting layer, and an electron-injecting layer are provided from an anode side is used. These functional layers are each formed using a material superior in its respective function. Characteristics of the light-emitting element depend not only on characteristics of the materials used for the functional layers but also on a combination or compatibility of the materials which are used. That is, even if a material with a good property is used, its favorable feature cannot be exhibited at all with an unsuitable combination; thus, it is very important to broaden choices of materials which can be used for each functional layer.

As for materials used for forming the light-emitting element, a comparatively large number of substances are proposed for hole-transporting materials. However, under the present circumstances, there are much fewer kinds and choices for electron-transporting materials and electron-injecting materials, compared to the hole-transporting materials.

In Reference 1 (Japanese Published Patent Application No. H10-340784), an example in which an acenaphtho[1,2-b]triphenylene derivative is used for an electron injecting and transporting layer is disclosed.

DISCLOSURE OF INVENTION

In view of the above, it is an object of the present invention to provide a new compound which is suitable for a material of an electron-transporting layer of a light-emitting element. In particular, it is an object to provide a compound which can be used for forming a light-emitting element capable of emitting light at a low drive voltage.

In the present invention, the above object is achieved by providing an acenaphthopyridine derivative represented by the following general formula (G1). Note that Het in the formula represents a pyridyl group or a quinolyl group.

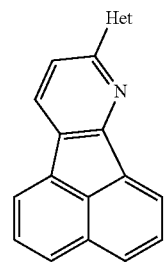

(G1)

As Het in the formula, specifically, any one of substituents represented by the following structural formulas (S1) to (S14) is given.

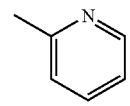

(S1)

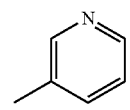

(S2)

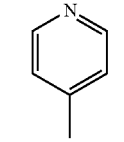

(S3)

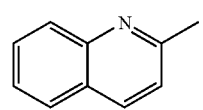

(S4)

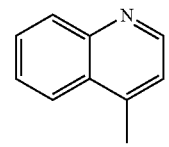

(S5)

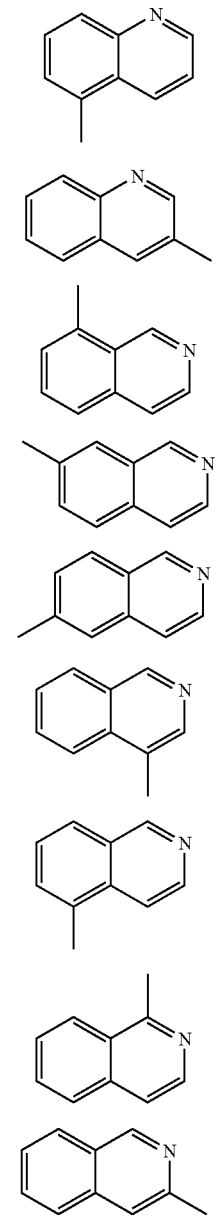

In addition, the present invention provides a material of a light-emitting element, which includes the acenaphthopyridine derivative.

In addition, the present invention provides a light-emitting element which includes the acenaphthopyridine derivative.

In addition, the present invention provides a light-emitting device and an electronic appliance, each of which includes the acenaphthopyridine derivative.

By using the acenaphthopyridine derivative according to the present invention for an electron-transporting layer of an organic EL element, a light-emitting element which can be driven at a low voltage can be manufactured, which is an excellent point of the acenaphthopyridine derivative according to the present invention.

BEST MODE FOR CARRYING OUT THE INVENTION

Figure 1A:
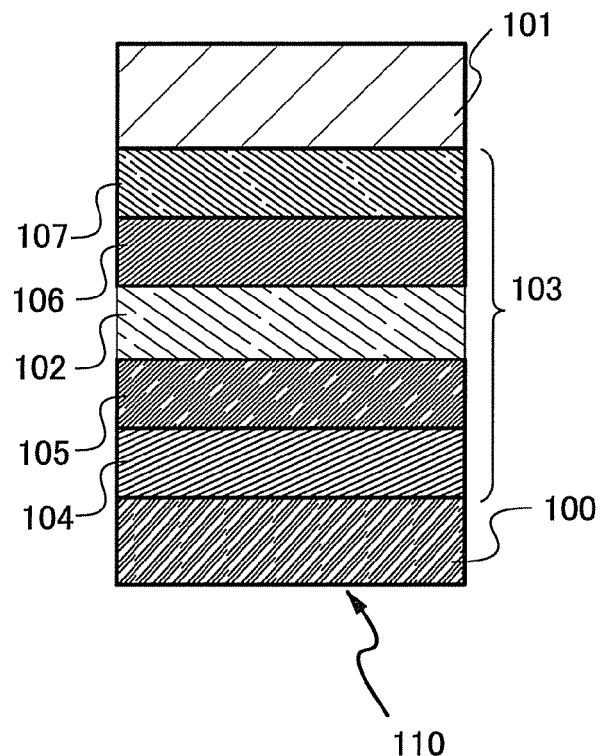
FIGS. 1A and 1B each illustrate a light-emitting element according to an embodiment of the present invention.

Hereinafter, embodiments of the present invention will be described. Note that the present invention can be implemented in a lot of different embodiments, and it is easily understood by those skilled in the art that modes and details thereof can be variously changed unless such changes depart from the spirit and the scope of the present invention. Therefore, the present invention should not be construed as being limited to the description of the embodiments.

Embodiment 1

The present inventors have synthesized a new acenaphthopyridine derivative represented by the following general formula (G1) and found that the acenaphthopyridine derivative exhibits an excellent electron-transporting property or an excellent electron-injecting property when being used for an electron-transporting layer or an electron-injecting layer of a light-emitting element.

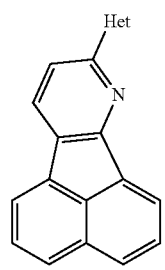

(G1)

In the general formula (G1), Het represents a pyridyl group or a quinolyl group. Specific examples of the pyridyl group and the quinolyl group include groups represented by the following structural formulas (S1) to (S14) and the like.

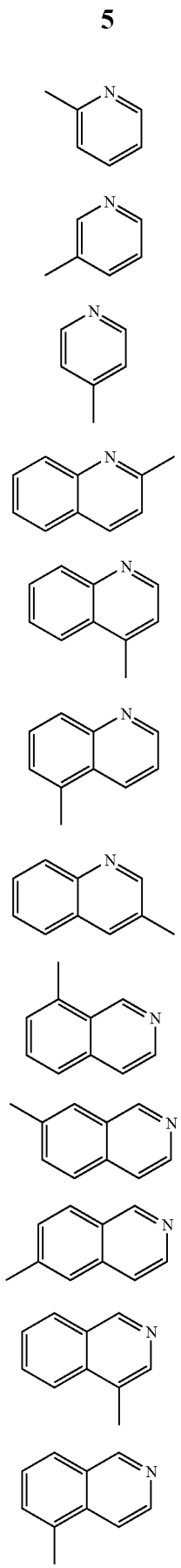

-continued

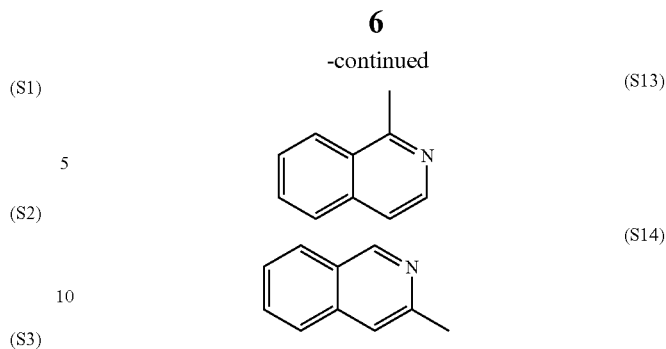

A method for synthesizing these acenaphthopyridine derivatives will be described below.

Step 1: Synthesis of Amidrazone Derivative

A heterocyclic compound (a compound A) having a nitrile group and hydrazine are stirred in a solvent, so that an amidrazone derivative (a compound B) can be obtained. In the formula, Het represents a heterocycle, which is a pyridyl group or a quinolyl group. The synthesis scheme of Step 1 is shown in (Ga-1).

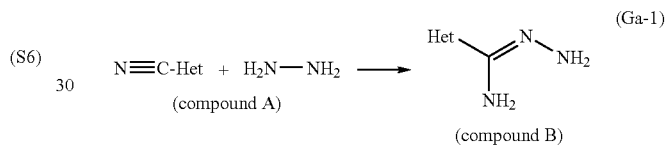

Hydrazine which is used here may be a hydrate. In addition, examples of the solvent which can be used in this reaction include alcohols such as ethanol, methanol, or butanol, aliphatic hydrocarbons such as hexan or cyclohexane, aromatic hydrocarbons such as benzene, toluene, or xylene, water, and the like. Note that the solvent which can be used is not limited to the above examples. Alcohols can be well mingled with hydrazine or a hydrate thereof and thus are preferably used. In the case of using a solvent other than alcohols, a solvent which can be mingled with hydrazine or a hydrate thereof is preferably used. However, the solvent is not necessarily used in this reaction.

Step 2: Synthesis of 7,8,10-triaza-fluoranthene Derivative

The amidrazone derivative (the compound B) synthesized in Step 1 and acenaphthene-1,2-dione are heated in a solvent, so that a 7,8,10-triaza-fluoranthene derivative (a compound C) can be synthesized. In the formula, Het represents a heterocycle, which is a pyridyl group or a quinolyl group. The synthesis scheme of Step 2 is shown in (Ga-2).

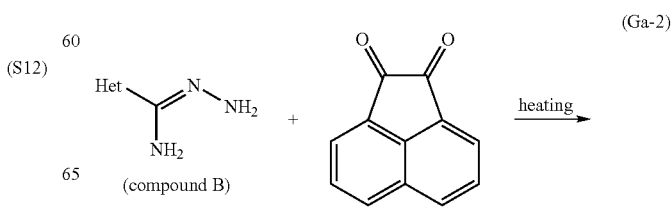

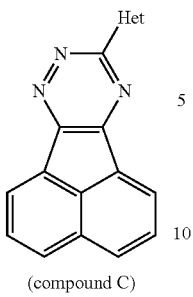

(compound C)

Examples of the solvent which can be used in this reaction include alcohols such as ethanol, methanol, or butanol, ethers such as tetrahydrofuran, diethyl ether, cyclopentyl methyl ether, or diisopropyl ether, aliphatic hydrocarbons such as hexane or cyclohexane, aromatic hydrocarbons such as benzene, toluene, or xylene, alkyl halides such as chloroform, dichloromethane, carbon tetrachloride, 1,2-dichloroethane, or 1,1,2,2,-tetrachloromethane, water, and the like. Note that the solvent which can be used is not limited to the above examples. Alcohols can be well mingled with the amidrazone derivative and thus are preferably used. In the case of using a solvent other than alcohols, a solvent which can be mingled with the amidrazone derivative is preferably used.

Step 3: Synthesis of Acenaphthopyridine Derivative

The 7,8,10-triaza-fluoranthene derivative (the compound C) and a compound having an alkene structure are heated in a solvent, so that the acenaphthopyridine derivative (G1) of this embodiment can be obtained. In the formula, Het represents a heterocycle, which is a pyridyl group or a quinolyl group. The synthesis scheme of Step 3 is shown in (Ga-3).

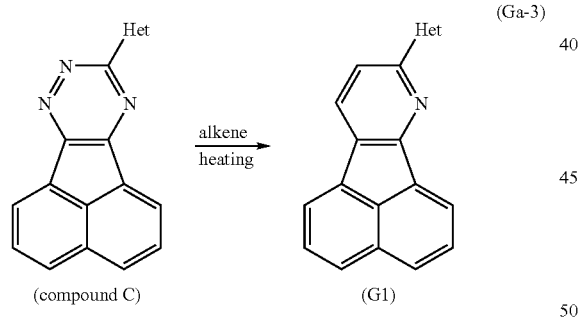

(compound C)                    (G1)

Examples of the solvent which can be used in this reaction include alcohols such as ethanol, methanol, or butanol, ethers such as tetrahydrofuran, diethyl ether, cyclopentyl methyl ether, or diisopropyl ether, aliphatic hydrocarbons such as hexane or cyclohexane, aromatic hydrocarbons such as benzene, toluene, or xylene, alkyl halides such as chloroform, dichloromethane, carbon tetrachloride, 1,2-dichloroethane, or 1,1,2,2,-tetrachloromethane, halogenated hydrocarbon such as chlorobenzen, bromobenzene, 1,2-dichlorobenzene, 1,3-dichlorobenzene, 1,4-dichlorobenzene, 1,2-dibromobenzene, 1,3-dibromobenzene, or 1,4-dibromobenzene, and the like. Note that the solvent which can be used is not limited to the above examples. Further, the solvent is not necessarily used in this reaction. The compound having an alkene structure can be bicyclo[2,2,1]hepta-2,5-diene or the like but is not limited thereto.

Specific examples of the acenaphthopyridine derivative represented by the above general formula (G1) are shown in the following structural formulas (1) to (14).

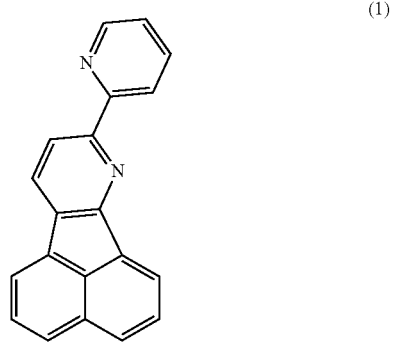

(1)

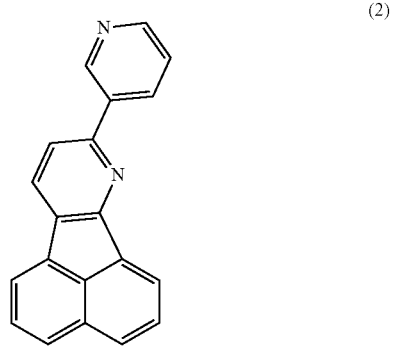

(2)

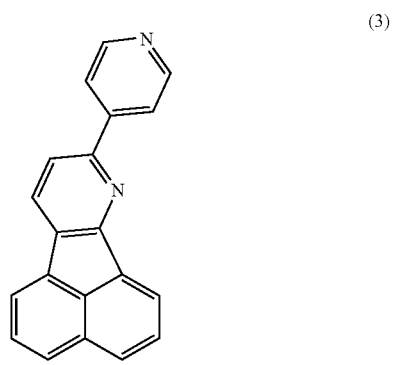

(3)

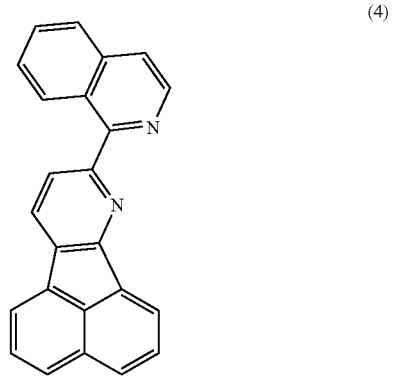

(4)

-continued
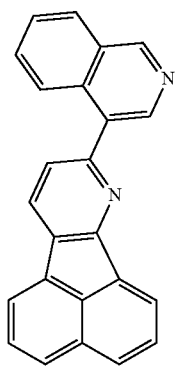
(5)
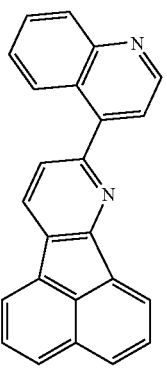
(6)
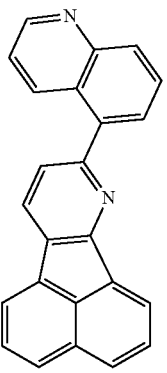
(7)
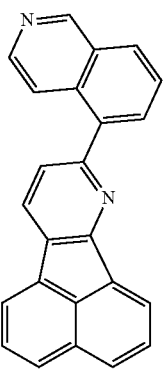
(8)
-continued
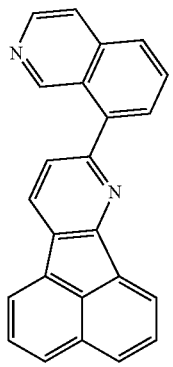
(9)
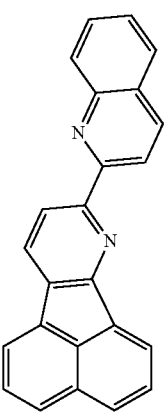
(10)
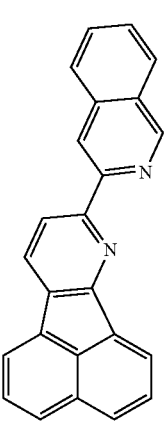
(11)
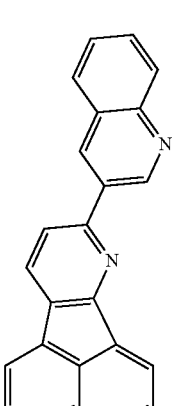
(12)

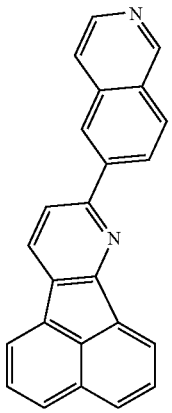

(13)

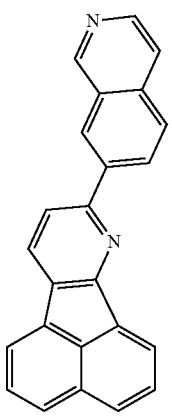

(14)

Embodiment 2

In this embodiment, a light-emitting element including the acenaphthopyridine derivative described in Embodiment 1 will be described along with a manufacturing method.

First, an anode 100 is formed over a base having an insulating surface. For the anode 100, a metal, an alloy, a conductive compound, a mixture thereof, or the like having a high work function (specifically, greater than or equal to 4.0 eV) is preferably used. Specifically, indium tin oxide (hereinafter also referred to as ITO), indium tin oxide including silicon or silicon oxide, indium oxide including zinc oxide (ZnO), indium oxide including tungsten oxide and zinc oxide (IWZO), or the like can be used. Although these conductive metal oxide films are generally formed by sputtering, they may be formed by applying a sol-gel method or the like. For example, indium oxide including zinc oxide (ZnO) can be deposited by a sputtering method using a target in which 1 to 20 wt % zinc oxide is added to indium oxide. In addition, indium oxide including tungsten oxide and zinc oxide (IWZO) can be deposited by a sputtering method using a target in which 0.5 to 5 wt % tungsten oxide and 0.1 to 1 wt % zinc oxide are included in indium oxide. Furthermore, gold (Au), platinum (Pt), nickel (Ni), tungsten (W), chromium (Cr), molybdenum (Mo), iron (Fe), cobalt (Co), copper (Cu), palladium (Pd), a nitride of the metal material (e.g., titanium nitride), or the like can be used.

Then, a layer 103 including an organic compound is formed. The layer 103 including an organic compound includes the acenaphthopyridine derivative described in Embodiment 1. Besides the acenaphthopyridine derivative, either a low-molecular material or a high-molecular material can be used. Note that the material for forming the layer 103 including an organic compound is not limited to an organic compound material, and may partly include an inorganic compound. In addition, the layer 103 including an organic compound is generally formed with a combination of functional layers each having its respective function as appropriate, such as a hole-injecting layer, a hole-transporting layer, a hole-blocking layer, a light-emitting layer, an electron-transporting layer, an electron-injecting layer, and the like. A layer having two or more functions of the above layers may be formed, or not all of the above layers may be formed. Naturally, a layer other than the above functional layers may be formed. The acenaphthopyridine derivative described in Embodiment 1 may be included in any of the functional layers. However, since the acenaphthopyridine derivative has an excellent electron-injecting property and an excellent electron-transporting property, it is preferably used for the electron-injecting layer or the electron-transporting layer.

In this embodiment, a light-emitting element is described as an example, in which, as the layer 103 including an organic compound, a hole-injecting layer 104, a hole-transporting layer 105, a light-emitting layer 102, an electron-transporting layer 106, and an electron-injecting layer 107 are stacked in this order from the anode 100 side as illustrated in FIG. 1A.

When the hole-injecting layer 104 is provided, a metal oxide such as vanadium oxide, molybdenum oxide, ruthenium oxide, or aluminum oxide can be used as the material thereof. Alternatively, if an organic compound is used, a porphyrin-based compound is effective, and phthalocyanine ($H_2Pc$), copper phthalocyanine (CuPc), or the like can be used. Furthermore, for the hole-injecting layer 104, a high-molecular compound (an oligomer, a dendrimer, a polymer, or the like) can be used. Examples of the high-molecular compound include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), poly[N,N'-bis(4-butylphenyl)-N,N'-bis(phenyl)benzidine (Poly-TPD), and the like. In addition, a high-molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used. The hole-injecting layer 104 is formed to be in contact with the anode 100. By providing the hole-injecting layer 104, a barrier to carrier injection can be lowered and carriers are efficiently injected to the light-emitting element; as a result, the drive voltage can be reduced.

In addition, for the hole-injecting layer 104, a material obtained by making a substance with a high hole-transporting property include an acceptor substance (hereinafter, a composite material) can be used. Note that, by using the composite material, the hole-injecting layer 104 can have an ohmic contact with the electrode and a material used to form the electrode can be selected regardless of its work function. In other words, besides a material with a high work function, a material with a work function that is not so high or a material with a low work function may also be used for the anode. As the acceptor substance, an organic compound or a transition metal oxide such as 7,7,8,8-tetracyano-2,3,5,6-tetrafluoroquinodimethane ($F_4$-TCNQ) or chloranil can be given. In addition, an oxide of a metal that belongs to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is preferable since its electron-accepting property is high. In particular, molybdenum oxide is particularly preferable because of its stability in the atmosphere, a low hygroscopic property, and easiness in handling.

Note that, in this specification, "composition" means not only a simple mixture of two materials but also a mixture of a plurality of materials which leads to a condition where electric charge is given and received among the materials.

For the substance with a high hole-transporting property used for the composite material, any of various compounds such as an aromatic amine compound, a carbazole derivative, aromatic hydrocarbon, and a high-molecular compound (an oligomer, a dendrimer, a polymer, or the like) can be used. The substance with a high hole-transporting property which can be used for the composite material is preferably a substance having a hole mobility of greater than or equal to $1\times10^{-6}$ cm$^2$/Vs. Further, other materials may also be used as long as a hole-transporting property thereof is higher than an electron-transporting property thereof. Organic compounds that can be used for the composite material are specifically given below.

For example, as the aromatic amine compound which can be used for the composite material, the following can be given: 4,4'-bis[N-(1-naphthyl)-N-phenylamino]biphenyl (NPB or α-NPD); N,N'-bis(4-methylphenyl)-N,N'-diphenyl-p-phenylenediamine (DTDPPA); 4,4'-bis[N-(4-diphenylamino-phenyl)-N-phenylamino]biphenyl (DPAB); N,N'-bis[4-[bis(3-methylphenyl)amino]phenyl]-N,N'-diphenyl-[1,1'-Biphenyl]-4,4'-diamine (DNTPD); 1,3,5-tris[N-(4-diphenylaminophenyl)-N-phenylamino]benzene (DPA3B); and the like.

As the carbazole derivative which can be used for the composite material, the following can be specifically given: 3-[N-(9-phenylcarbazol-3-yl)-N-phenylamino]-9-phenyl-carbazole (PCzPCA1); 3,6-bis[N-(9-phenylcarbazol-3-yl)-N-phenylamino]-9-phenylcarbazole (PCzPCA2); 3-[N-(1-naphthyl)-N-(9-phenylcarbazol-3-yl)amino]-9-phenylcarbazole (PCzPCN1); 4,4'-di(N-carbazolyl)biphenyl (CBP); 1,3,5-tris[4-(N-carbazolyl)phenyl]benzene (TCPB); 9-[4-(10-phenyl-9-anthryl)phenyl]-9H-carbazole (CzPA); 1,4-bis[4-(N-carbazolyl)phenyl]-2,3,5,6-tetraphenylbenzene; and the like.

As the aromatic hydrocarbon which can be used for the composite material, for example, the following can be given: 2-tert-butyl-9,10-di(2-naphthyl)anthracene (t-BuDNA); 2-tert-butyl-9,10-di(1-naphthyl)anthracene, 9,10-bis(3,5-diphenylphenyl)anthracene (DPPA); 2-tert-butyl-9,10-bis(4-phenylphenyl)anthracene (t-BuDBA); 9,10-di(2-naphthyl)anthracene (DNA); 9,10-diphenylanthracene (DPAnth); 2-tert-butylanthracene (t-BuAnth); 9,10-bis(4-methyl-1-naphthyl)anthracene (DMNA); 9,10-bis[2-(1-naphthyl)phenyl]-2-tert-butyl-anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these, pentacene, coronene, and the like can also be given. As described here, the aromatic hydrocarbon which has a hole mobility of greater than or equal to $1\times10^{-6}$ cm$^2$/Vs and which has 14 to 42 carbon atoms is particularly preferable.

The aromatic hydrocarbon which can be used for the composite material may have a vinyl skeleton. As the aromatic hydrocarbon having a vinyl group, for example, the following can be given: 4,4'-bis(2,2-diphenylvinyl)biphenyl (DPVBi); 9,10-bis[4-(2,2-diphenylvinyl)phenyl]anthracene (DPVPA); and the like.

In addition, as the material of the hole-injecting layer, the composite material is formed using the above-described high-molecular compound such as PVK, PVTPA, PTPDMA, or poly-TPD and the above-described acceptor substance, and the composite material may be used to form the hole-injecting layer 104.

When the composite material as described above is used for the hole-injecting layer 104, various kinds of metals, alloys, electrically conductive compounds, a mixture thereof, or the like can be used for the anode 100, regardless of its work function. Therefore, for example, aluminum (Al), silver (Ag), an alloy including aluminum (e.g., AlSi), or the like can be used for the anode, in addition to the above-described materials. In addition, an element belonging to Group 1 or Group 2 of the periodic table, which is a low-work-function material, that is, an alkali metal such as lithium (Li) or cesium (Cs), an alkaline earth metal such as magnesium (Mg), calcium (Ca), or strontium (Sr), an alloy including any of these metals (e.g., MgAg or AlLi), a rare earth metal such as europium (Eu) or ytterbium (Yb), an alloy including such a rare earth metal, or the like can be used. A film of an alkali metal, an alkaline earth metal, or an alloy including these can be formed by a vacuum evaporation method. In addition, a film of an alloy including an alkali metal or an alkaline earth metal can also be formed by a sputtering method. Moreover, silver paste or the like can be deposited by an ink-jet method or the like.

For the hole-transporting layer 105, an appropriate material such as N,N'-bis(spiro-9,9'-bifluoren-2-yl)-N,N'-diphenylbenzidine (BSPB); 4,4'-bis[N-(1-naphthyl)-N-phenylamino]biphenyl (NPB or α-NPD); 4,4'-bis[N-(3-methylphenyl)-N-phenylamino]biphenyl (TPD); 4,4',4"-tris(N,N-diphenylamino)triphenylamine (TDATA); 4,4',4"-tris[N-(3-methylphenyl)-N-phenylamino]triphenylamine (MTDATA); N,N'-bis[4-[bis(3-methylphenyl)amino]phenyl]-N,N'-diphenyl-[1,1'-Biphenyl]-4,4'-diamine (DNTPD); 1,3,5-tris[N,N-di(m-tolyl)amino]benzene (m-MTDAB); 4,4',4"-tris(N-carbazolyl)triphenylamine (TCTA); phthalocyanine (H$_2$Pc); copper phthalocyanine (CuPc); or vanadyl phthalocyanine (VOPc) can be used. Although a substance having a hole mobility of greater than or equal to $1\times10^{-6}$ cm$^2$/Vs is preferably used for the hole-transporting layer, any substance can be used for the hole-transporting layer as long as a hole-transporting property thereof is higher than an electron-transporting property thereof. Moreover, the hole-transporting layer is not limited to a single-layer structure, and may be formed as a multilayer structure in which two or more layers formed of substances which satisfy the above-described conditions are combined. The hole-transporting layer can be formed by a vacuum evaporation method or the like.

As the hole-transporting layer 105, the high-molecular compound such as PVK, PVTPA, PTPDMA, or Poly-TPD which is mentioned as the material of the hole-injecting layer 104 can also be used. In this case, a solution process such as an ink-jet method or a spin coating method can be used.

The light-emitting layer 102 may be formed using a film including only a light-emitting substance or a film in which an emission center substance is dispersed in a host material.

A material which can be used as the light-emitting substance or the emission center substance in the light-emitting layer 102 is not limited to a particular material, and light emitted from the material may be either fluorescence or phosphorescence. The following can be given as examples of the light-emitting substance or the emission center substance. As examples of a substance which exhibits blue light emission (light emission wavelength: 400 to 480 nm), there are N,N'-bis[4-(9H-carbazol-9-yl)phenyl]-N,N'-diphenylstilbene-4, 4'diamine (YGA2S); 4-(9H-carbazol-9-yl)-4'-(10-phenyl-9-anthryl)triphenylamine (YGAPA); 4-(9H-carbazol-9-yl)-4'-(9,10-diphenyl-2-anthryl)triphenylamine (2YGAPPA); N,9-diphenyl-N-[4-(10-phenyl-9-anthryl)phenyl]-9H-carbazole-3-amine (PCAPA); perylene; 2,5,8,11-tetra-(tert-butyl) perylene (TBP); and the like. In addition, materials which emit phosphorescence, such as bis[2-(4',6'-difluorophenyl)pyridinato-N,C$^{2'}$]iridium(III)tetrakis(1-pyrazolyl)borate (FIr6) and bis[2-(4',6'-difluorophenyl)pyridinato-N,C$^{2'}$]iridium(III)picolinate (FIrpic) can also be used. As examples of a substance which exhibits blue green light emission (light emission wavelength: 480 to 520 nm), there are N,N"-(2-tert-butylanthracene-9,10-diyldi-4,1-phenylene)bis[N,N',N'-triphenyl-1,4-phenylenediamine] (DPABPA); N,9-diphenyl-N-[4-(9,10-diphenyl-2-anthryl)phenyl]-9H-carbazole-3-amine (2PCAPPA); N-[4-(9,10-diphenyl-2-anthryl)phenyl]-N,N',N'-triphenyl-1,4-phenyldiamine (2DPAPPA); N,N,N',N',N",N",N"',N"'-octaphenyldibenzo[g,p]chrysene-2,7,10,15-tetramine (DBC1); coumarin 30; and the like. In addition, materials which emit phosphorescence, such as bis[2-(3',5'bistrifluoromethylphenyl)pyridinato-N,C$^{2'}$]iridium(III)picolinate (Ir(CF$_3$ppy)$_2$(pic)); and bis[2-(4',6'-difluorophenyl)pyridinato-N,C$^{2'}$]iridium(III)acetylacetonate (FIracac) can also be used. As examples of a substance which exhibits yellow light emission (light emission wavelength: 540 to 600 nm), there are rubrene; 5,12-bis(1,1'-biphenyl-4-yl)-6,11-diphenyltetracene (BPT); 2-(2-{2-[4-(dimethylamino)phenyl]ethenyl}-6-methyl-4H-pyran-4-ylidene)propanedinitrile (DCM1); 2-{2-methyl-6-[2-(2,3,6,7-tetrahydro-1H,5H-benzo[ij]quinolizin-9-yl)ethenyl]-4H-pyran-4-ylidene}propanedinitrile (DCM2); and the like. In addition, materials which emit phosphorescence, such as bis(benzo[h]quinolinato)iridium(III)acetylacetonate (Ir(bzq)$_2$(acac)); bis(2,4-diphenyl-1,3-oxazolato-N,C$^{2'}$)iridium(III)acetylacetonate (Ir(dpo)$_2$(acac)); bis[2-(4'-perfluorophenylphenyl)pyridinato]iridium(III)acetylacetonate (Ir(p-PF-ph)$_2$(acac)); and bis(2-phenylbenzothiazolato-N,C$^{2'}$)iridium(III)acetylacetonate (Ir(bt)$_2$(acac)) can also be used. As examples of a substance which exhibits red light emission (light emission wavelength: 600 to 700 nm), there are N,N,N',N'-tetrakis(4-methylphenyl)tetracene-5,11-diamine (p-mPhTD); 7,13-diphenyl-N,N,N',N'-tetrakis(4-methylphenyl)acenaphtho[1,2-a]fluoranthene-3,10-diamine (p-mPhAFD); 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (DCJTI); 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (DCJTB); 2-(2,6-bis{2-[4-(dimethylamino)phenyl]ethenyl}-4H-pyran-4-ylidene)propanedinitrile (BisDCM); 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (BisDCJTM); and the like. In addition, materials which emit phosphorescence, such as bis[2-(2'-benzo[4,5-α]thienyl)pyridinato-N,C$^{3'}$]iridium(III) acetylacetonate (Ir(btp)$_2$(acac)); bis(1-phenylisoquinolinato-N,C$^{2'}$)iridium(III)acetylacetonate (Ir(piq)$_2$(acac)); (acetylacetonato)bis[2,3-bis(4-fluorophenyl)quinoxalinato] iridium(III) (Ir(Fdpq)$_2$(acac)); 2,3,7,8,12,13,17,18-octaethyl-21H,23H-porphyrinplatinum(II) (PtOEP); tris(1,3-diphenyl-1,3-propanedionato)(monophenanthroline) europium(III) (Eu(DBM)$_3$(Phen)); and tris[1-(2-thenoyl)-3,3,3-trifluoroacetonato](monophenanthroline)europium (III) can also be used.

Examples of a material which can be used as the host material include, but not limited to, the following materials:

metal complexes such as tris(8-quinolinolato)aluminum(III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato) aluminum(III) (BAlq), bis(8-quinolinolato)zinc(II) (Znq), bis[2-(2-benzoxazolyl)phenolato]zinc(II) (ZnPBO), and bis [2-(2-benzothiazolyl)phenolato]zinc(II) (ZnBTZ); heterocyclic compounds such as 2-(4-biphenylyl)-5-(4-tert-butylphenyl)-1,3,4-oxadiazole (PBD), 1,3-bis[5-(p-tert-butylphenyl)-1,3,4-oxadiazol-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), bathocuproine (BCP), and 9-[4-(5-phenyl-1,3,4-oxadiazol-2-yl)phenyl]-9H-carbazole (CO11); and aromatic amine compounds such as NPB (or α-NPD), TPD, and BSPB. In addition, condensed polycyclic aromatic compounds such as anthracene derivatives, phenanthrene derivatives, pyrene derivatives, chrysene derivatives, and dibenzo[g,p]chrysene derivatives are given. The following is specifically given as the condensed polycyclic aromatic compound: 9,10-diphenylanthracene (DPAnth); N,N-diphenyl-9-[4-(10-phenyl-9-anthryl)phenyl]-9H-carbazole-3-amine (CzAlPA); 4-(10-phenyl-9-anthryl)triphenylamine (DPhPA); 4-(9H-carbazol-9-yl)-4'-(10-phenyl-9-anthryl)triphenylamine (YGAPA); N,9-diphenyl-N-[4-(10-phenyl-9-anthryl)phenyl]-9H-carbazole-3-amine (PCAPA); N,9-diphenyl-N-{4-[4-(10-phenyl-9-anthryl)phenyl]phenyl}-9H-carbazole-3-amine (PCAPBA); N,9-diphenyl-N-(9,10-diphenyl-2-anthryl)-9H-carbazole-3-amine (2PCAPA); 6,12-dimethoxy-5,11-diphenylchrysene, N,N,N',N',N",N",N"',N"'-octaphenyldibenzo[g,p]chrysene-2,7,10,15-tetramine (DBC1); 9-[4-(10-phenyl-9-anthryl)phenyl]-9H-carbazole (CzPA); 3,6-diphenyl-9-[4-(10-phenyl-9-antryl)phenyl]-9H-carbazole (DPCzPA); 9,10-bis(3,5-diphenylphenyl)anthracene (DPPA); 9,10-di(2-naphthyl) anthracene (DNA); 2-tert-butyl-9,10-di(2-naphthyl) anthracene (t-BuDNA); 9,9'-bianthryl (BANT); 9,9'-(stilbene-3,3'-diyl)diphenanthrene (DPNS); 9,9'-(stilbene-4,4'-diyl)diphenanthrene (DPNS2); 3,3',3"-(benzene-1,3,5-triyl)tripyrene (TPB3); and the like. A substance having an energy gap which is larger than that of the emission center substance may be selected from these substances and known substances. Moreover, in the case where the emission center substance emits phosphorescence, a substance having triplet energy (energy difference between a ground state and a triplet excitation state) which is higher than that of the emission center substance may be selected as the host material.

The light-emitting layer 102 can also be formed using two or more layers. For example, in the case where a first light-emitting layer and a second light-emitting layer are stacked from the hole-transporting layer side to form the light-emitting layer 102, a hole-transporting substance may be used for a host material of the first light-emitting layer and an electron-transporting substance may be used for a host material of the second light-emitting layer.

The light-emitting layer having the above-described structure can be formed by a vacuum evaporation method or the like.

In the case where the electron-transporting layer 106 is provided, it is disposed between the light-emitting layer 102 and the electron-injecting layer 107 or a cathode. The electron-transporting layer 106 is preferably formed using the acenaphthopyridine derivative described in Embodiment 1. The acenaphthopyridine derivative described in Embodiment 1 exhibits an excellent electron-transporting property and is thus preferably used for the electron-transporting layer of the light-emitting element, which leads to reduction in drive voltage of the light-emitting element.

Examples of other materials suitable for the electron-transporting layer 106 include metal complexes having a quinoline skeleton or a benzoquinoline skeleton, such as tris(8-quinolinolato)aluminum (Alq), tris(4-methyl-8-quinolinolato)aluminum (Almq), bis(10-hydroxybenzo[h]-quinolinato)beryllium (BeBq$_2$), and bis(2-methyl-8-quinolinolato)-(4-phenylphenolato)aluminum (BAlq). Besides these materials, metal complexes having an oxazole ligand or a thiazole ligand, such as bis[2-(2-hydroxyphenyl)-benzoxazolato]zinc (Zn(BOX)2) and bis[2-(2-hydroxyphenyl)-benzothiazolato] zinc (Zn(BTZ)$_2$) can also be given. Furthermore, besides the metal complexes, 2-(4-biphenylyl)-5-(4-tert-butylphenyl)-1, 3,4-oxadiazole (PBD), 1,3-bis[5-(p-tert-butylphenyl)-1,3,4-oxadiazol-2-yl]benzene (OXD-7), bathophenanthroline (BPhen), bathocuproine (BCP), or the like can also be used. Although a substance having an electron mobility of greater than or equal to $1\times10^{-6}$ cm$^2$/Vs is preferably used for the electron-transporting layer, any substance can be used for the electron-transporting layer as long as an electron-transporting property thereof is higher than a hole-transporting property thereof. Moreover, the electron-transporting layer is not limited to a single-layer structure, and may be formed as a multilayer structure in which two or more layers formed of substances which satisfy the above-described conditions are combined. The electron-transporting layer can be formed by a vacuum evaporation method or the like.

Alternatively, a high-molecular compound can be used for the electron-transporting layer. For example, poly[(9,9-dihexylfluorene-2,7-diyl)-co-(pyridine-3,5-diyl)] (PF-Py), poly[(9,9-dioctyllfluorene-2,7-diyl)-co-(2,2'-bipyridine-6, 6'-diyl)] (PF-BPy), or the like can be used. In this case, a solution process such as an ink-jet method or a spin coating method can be used.

Note that a substance having a larger energy gap (or triplet energy) than that of the emission center substance of the light-emitting layer 102 is preferably used for the electron-transporting layer 106 in contact with the light-emitting layer 102. With such a structure, energy transfer from the light-emitting layer 102 to the electron-transporting layer 106 can be suppressed, and high emission efficiency can be achieved.

In the case where the electron-injecting layer 107 is provided, it is disposed being in contact with the cathode. By providing the electron-injecting layer, a barrier to carrier injection can be lowered and carriers are efficiently injected to the light-emitting element; as a result, the drive voltage can be reduced. The electron-transporting layer 107 is preferably formed using the acenaphthopyridine derivative described in Embodiment 1. The acenaphthopyridine derivative described in Embodiment 1 exhibits an excellent electron-injecting property and is thus preferably used for the electron-injecting layer of the light-emitting element, which leads to effective reduction in drive voltage of the light-emitting element.

When the electron-injecting layer 107 is formed using other materials, an alkali metal compound or an alkaline earth metal compound such as calcium fluoride, lithium fluoride, lithium oxide, or lithium chloride, or the like is preferable. Alternatively, a layer in which a so-called electron-transporting material such as tris(8-quinolinorato)aluminum (Alq$_3$) or bathocuproine (BCP) is combined with an alkali metal or an alkaline earth metal such as lithium or magnesium can also be used. It is preferable to use the layer in which an electron-transporting substance is combined with an alkali metal or an alkaline earth metal as the electron-injecting layer, since electron injection from the cathode efficiently proceeds. The electron-injecting layer can be formed by a vacuum evaporation method or the like. Moreover, when the electron-injecting layer 107 is provided, any of a variety of conductive materials such as Al, Ag, ITO, and indium oxide-tin oxide including silicon or silicon oxide can be used for the cathode, regardless of its work function.

Note that the layer 103 including an organic compound can be formed by either a wet process or a dry process, such as an evaporation method, an ink-jet method, a spin coating method, or a dip coating method, as well as the above-described formation method.

After that, a cathode 101 is formed, so that a light-emitting element 110 is completed. As the cathode 101, a metal, an alloy, a conductive compound, a mixture thereof, or the like having a low work function (specifically, less than or equal to 3.8 eV) is preferably used. Specifically, a metal belonging to Group 1 or Group 2 of the periodic table, that is, an alkali metal such as lithium (Li) or cesium (Cs); an alkaline earth metal such as magnesium (Mg), calcium (Ca), or strontium (Sr); an alloy including any of these metals (such as MgAg or AlLi); a rare earth metal such as europium (Er) or ytterbium (Yb); an alloy including the rare earth metal; or the like can be used. A film of an alkali metal, an alkaline earth metal, or an alloy including these can be formed by a vacuum evaporation method. In addition, an alloy including an alkali metal or an alkaline earth metal can also be formed by a sputtering method. Further, silver paste or the like can be deposited by an ink-jet method. Moreover, by providing the electron-injecting layer 107 between the cathode 101 and the electron-transporting layer 106, any of a variety of conductive materials such as Al, Ag, ITO, and indium oxide-tin oxide including silicon or silicon oxide can be used, regardless of its work function.

Note that a conductive composition including a conductive high molecule (also referred to as a conductive polymer) can also be used for the anode 100 or the cathode 101. When a thin film of the conductive composition is formed as the anode 100 or the cathode 101, the thin film preferably has a sheet resistance of less than or equal to 10000 Ω/square and a light transmittance of greater than or equal to 70% at a wavelength of 550 nm. Note that the resistivity of the conductive high molecule which is included in the thin film is preferably less than or equal to 0.1 Ω·cm.

As the conductive high molecule, a so-called π-electron conjugated conductive high molecule can be used. For example, polyaniline and/or a derivative thereof, polypyrrole and/or a derivative thereof, polythiophene and/or a derivative thereof, and a copolymer of two or more kinds of them can be given.

As specific examples of the conjugated conductive high molecule, the following can be given: polypyrrole; poly(3-methylpyrrole); poly(3-butylpyrrole); poly(3-octylpyrrole); poly(3-decylpyrrole); poly(3,4-dimethylpyrrole); poly(3,4-dibutylpyrrole); poly(3-hydroxypyrrole); poly(3-methyl-4-hydroxypyrrole); poly(3-methoxypyrrole); poly(3-ethoxypyrrole); poly(3-octoxypyrrole); poly(3-carboxypyrrole); poly(3-methyl-4-carboxypyrrole); polyN-methylpyrrole; polythiophene; poly(3-methylthiophene); poly(3-butylthiophene); poly(3-octylthiophene); poly(3-decylthiophene); poly(3-dodecylthiophene); poly(3-methoxythiophene); poly (3-ethoxythiophene); poly(3-octoxythiophene); poly(3-carboxythiophene); poly(3-methyl-4-carboxylthiophene); poly (3,4-ethylenedioxythiophene); polyaniline; poly(2-methylaniline); poly(2-octylaniline); poly(2-isobutylaniline); poly(3-isobutylaniline); poly(2-aniline sulfonic acid); poly(3-aniline sulfonic acid); and the like.

One of the above-described conductive high molecules can be used alone for the anode 100 or the cathode 101, or an organic resin may be added to such a conductive high molecule in order to adjust film characteristics and the conductive high molecule may be used as a conductive composition for the anode 100 or the cathode 101.

As for the organic resin, as long as the resin is compatible with the conductive high molecule or the resin can be mixed and dispersed into the conductive high molecule, a thermosetting resin, a thermoplastic resin, or a photocurable resin may be used. Examples of the organic resin are given below: a polyester-based resin such as polyethylene terephthalate, polybutylene terephthalate, or polyethylene naphthalate; a polyimide-based resin such as polyimide or polyamide imide; a polyamide resin such as polyamide 6, polyamide 6,6, polyamide 12, or polyamide 11; a fluorine resin such as polyvinylidene fluoride, polyvinyl fluoride, polytetrafluoroethylene, ethylene tetrafluoroethylene copolymer, or polychlorotrifluoroethylene; a vinyl resin such as polyvinyl alcohol, polyvinyl ether, polyvinyl butyral, polyvinyl acetate, or polyvinyl chloride; an epoxy resin; a xylene resin; an aramid resin; a polyurethane-based resin; a polyurea-based resin; a melamine resin; a phenol-based resin; polyether; an acrylic-based resin; a copolymer of any of these resins; and the like.

Furthermore, in order to adjust electric conductivity of the conductive high molecule or the conductive composition, the conductive high molecule or the conductive composition may be doped with an acceptor dopant or a donor dopant so that oxidation-reduction potential of a conjugated electron in the conjugated conductive high molecule may be changed.

As the acceptor dopant, a halogen compound, an organic cyano compound, an organic metal compound, or the like can be used. As examples of the halogen compound, chlorine, bromine, iodine, iodine chloride, iodine bromide, iodine fluoride, and the like can be given. As the organic cyano compound, a compound in which two or more cyano groups are included in a conjugated bond can be used. In addition, phosphorus pentafluoride, arsenic pentafluoride, antimony pentafluoride, boron trifluoride, boron trichloride, boron tribromide, or the like; inorganic acid such as hydrochloric acid, sulfuric acid, nitric acid, phosphoric acid, fluoroboric acid, hydrofluoric acid, or perchloric acid; or organic acid such as organic carboxylic acid or organic sulfonic acid can also be used. As the organic carboxylic acid and the organic sulfonic acid, the above-described carboxylic acid compounds and sufonic acid compounds can be used. For example, tetracyanoethylene, tetracyanoethylene oxide, tetracyanobenzene, tetracyanoquinodimethane, tetracyano azanaphthalene, or the like can be used.

As the donor dopant, an alkali metal, an alkaline earth metal, a quaternary amine compound, and the like can be given.

Further, a thin film to be the anode 100 or the cathode 101 can be formed by a wet process using a solution in which the conductive high molecule or the conductive composition is dissolved in water or an organic solvent (e.g., an alcohol-based solvent, a ketone-based solvent, an ester-based solvent, a hydrocarbon-based solvent, or an aromatic solvent).

The solvent for dissolving the conductive high molecule or the conductive composition is not limited to a particular solvent, and a solvent which dissolves the above-described conductive high molecule and a high-molecular resin compound such as an organic resin may be used. For example, the conductive high molecule or the conductive composition may be dissolved in a single solvent or a mixed solvent of any of the following: water, methanol, ethanol, propylene carbonate, N-methylpyrrolidone, dimethylformamide, dimethylacetamide, cyclohexanone, acetone, methylethylketone, methylisobutylketone, toluene, and the like.

After the conductive composition is dissolved in a solvent as described above, a film thereof can be formed by a wet process such as an application method, a coating method, a droplet discharge method (also referred to as an ink-jet method), or a printing method. The solvent may be dried by heat treatment or may be dried under reduced pressure. In the case where the organic resin is a thermosetting resin, heat treatment may be further performed. Further, in the case where the organic resin is a photocurable resin, light irradiation treatment may be performed.

Note that by varying the materials of the anode 100 and the cathode 101, the light-emitting element of this embodiment can have a variety of structures. For example, with the anode 100 having a light-transmitting property, light is emitted from the anode 100 side, whereas with the anode 100 having a light-blocking property (reflectivity, in particular) and the cathode 101 having a light-transmitting property, light is emitted from the cathode 101 side. Furthermore, with both the anode 100 and the cathode 101 having a light-transmitting property, light can be emitted from both the anode side and the cathode side.

Since the acenaphthopyridine derivative described in Embodiment 1 is used for the light-emitting element of this embodiment as described above, the drive voltage of the light-emitting element can be reduced. In particular, when the acenaphthopyridine derivative described in Embodiment 1 is used for the electron-transporting layer or the electron-injecting layer, or both of them of the light-emitting element of this embodiment, the drive voltage of the light-emitting element can be effectively reduced.

Embodiment 3

In this embodiment, an embodiment of a light-emitting element with a structure in which a plurality of light-emitting units are stacked (hereinafter also referred to as a stacked element) will be described with reference to FIG. 1B. This light-emitting element has a plurality of light-emitting units between a first electrode and a second electrode. Each light-emitting unit can have a structure similar to that of the layer 103 including an organic compound described in Embodiment 2. That is, the light-emitting element described in Embodiment 2 is a light-emitting element having one light-emitting unit, whereas a light-emitting element described in this embodiment has a plurality of light-emitting units.

Figure 1B:
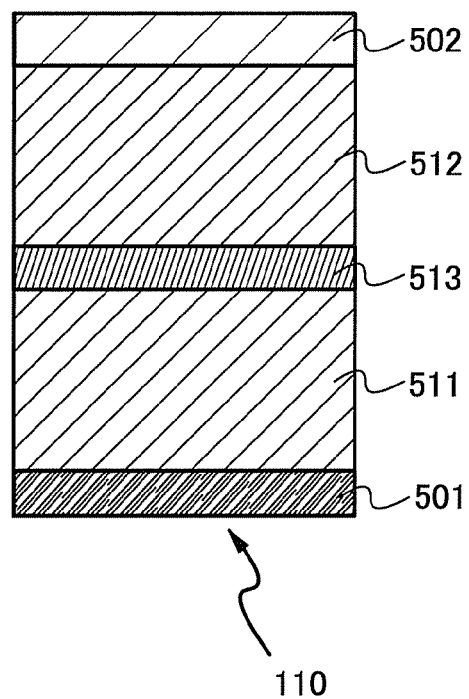

In FIG. 1B, a first light-emitting unit 511 and a second light-emitting unit 512 are stacked between a first electrode 501 and a second electrode 502, and a charge-generating layer 513 is provided between the first light-emitting unit 511 and the second light-emitting unit 512. The first electrode 501 and the second electrode 502 correspond to the anode 100 and the cathode 101 of Embodiment 2, respectively, and can be formed using materials similar to those described in Embodiment 2. In addition, the first light-emitting unit 511 and the second light-emitting unit 512 may have the same structure or different structures.

The charge-generating layer 513 includes a composite material of an organic compound and a metal oxide. This composite material of an organic compound and a metal oxide has been described in Embodiment 2 and includes an organic compound and a metal oxide such as vanadium oxide, molybdenum oxide, or tungsten oxide. As the organic compound, any of a variety of compounds such as an aromatic amine compound, a carbazole derivative, aromatic hydrocarbon, and a high-molecular compound (an oligomer, a dendrimer, a polymer, or the like) can be used. Note that an organic compound having a hole mobility of greater than or equal to $1\times10^{-6}$ cm$^2$/Vs is preferably applied as a hole-transporting organic compound. Other substances may also be used as long as hole-transporting properties thereof are higher than electron-transporting properties thereof. The composite of an organic compound and a metal oxide is superior in carrier-injecting property and carrier-transporting property and, accordingly, low-voltage driving and low-current driving can be realized.

Note that the charge-generating layer 513 may also be formed by combining a layer including the composite material of an organic compound and a metal oxide with a layer formed using other materials. For example, the charge-generating layer 513 may be formed with a combination of a layer including the composite material of an organic compound and a metal oxide with a layer including one compound selected from electron-donating substances and a compound having a high electron-transporting property. Further, the charge-generating layer 513 may be formed with a combination of a layer including the composite material of an organic compound and a metal oxide with a transparent conductive film.

In any case, the charge-generating layer 513 interposed between the first light-emitting unit 511 and the second light-emitting unit 512 may be formed using a material by which electrons are injected to one light-emitting unit and holes are injected to the other light-emitting unit when a voltage is applied to the first electrode 501 and the second electrode 502. For example, when a voltage is applied so that a potential of the first electrode is higher than that of the second electrode in FIG. 1B, any structure is acceptable for the charge-generating layer 513 as long as the charge-generating layer 513 injects electrons and holes to the first light-emitting unit 511 and the second light-emitting unit 512, respectively.

Although the light-emitting element having two light-emitting units is described in this embodiment, a light-emitting element in which three or more light-emitting units are stacked can be employed in a similar way. By arranging a plurality of light-emitting units that are partitioned by a charge-generating layer between a pair of electrodes, like the light-emitting element of this embodiment, the long lifetime of the element can be realized in a high-luminance region, while keeping current density low. In the case where the light-emitting element is applied to lighting as an application example, voltage drop due to resistance of an electrode material can be reduced. Accordingly, light can be uniformly emitted in a large area. Moreover, a light-emitting device with low power consumption, which can be driven at low voltage, can be achieved.

In addition, by making colors of light emitted from the light-emitting units different from each other, light emission of a desired color can be obtained as the whole light-emitting element. For example, in a light-emitting element having two light-emitting units, the emission colors of the first light-emitting unit and the second light-emitting unit are made complementary, so that a light-emitting element which emits white light as a whole light-emitting element can be obtained. Note that "complementary color" means a relation between colors which becomes an achromatic color when they are mixed. That is, white light emission can be obtained by mixture of light obtained from substances emitting light of complementary colors. The same can be applied to a light-emitting element having three light-emitting units. For example, when a first light-emitting unit emits red light, a second light-emitting unit emits green light, and a third light-emitting unit emits blue light, white light can be emitted from the whole light-emitting element.

Since the acenaphthopyridine derivative described in Embodiment 1 is used for the light-emitting element of this embodiment, the drive voltage of the light-emitting element can be reduced.

Note that this embodiment can be combined with any of other embodiments as appropriate.

Embodiment 4

In this embodiment, an embodiment in which the acenaphthopyridine derivative described in Embodiment 1 is used for an active layer of a vertical transistor (SIT) that is one kind of an organic semiconductor element will be described as an example.

Figure 2:
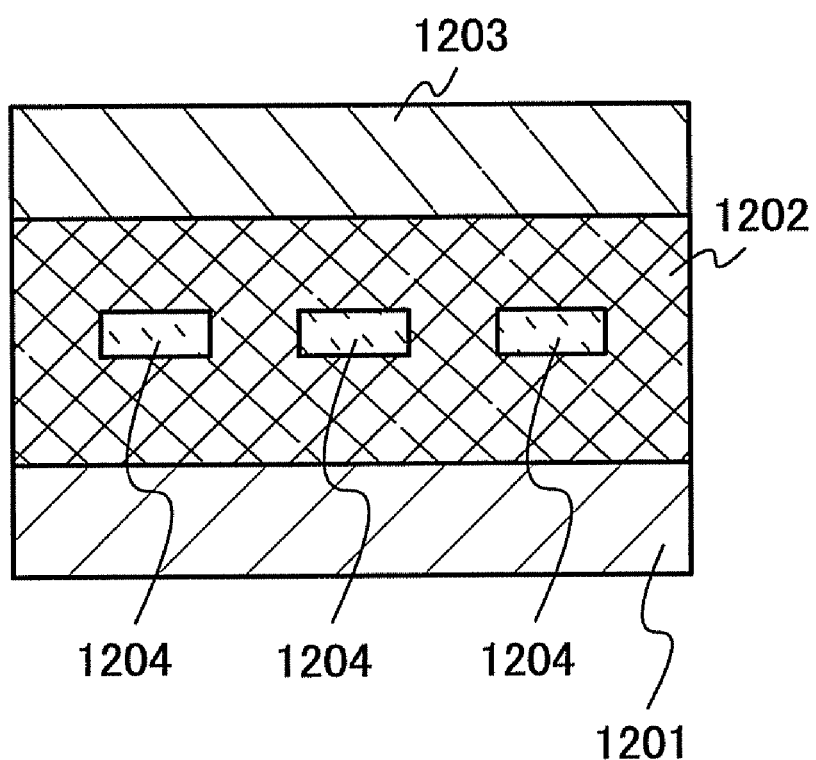
FIG. 2 illustrates an organic semiconductor element according to an embodiment of the present invention.

As illustrated in FIG. 2, an element has a structure in which a thin-film active layer 1202 including the acenaphthopyridine derivative according to the present invention is sandwiched between a source electrode 1201 and a drain electrode 1203, and a gate electrode 1204 is embedded in the active layer 1202. The gate electrode 1204 is electrically connected to a unit (means) for applying a gate voltage, and the source electrode 1201 and the drain electrode 1203 are electrically connected to a unit (means) for controlling a source-drain voltage.

In such an element structure, when a voltage is applied between the source and the drain under the condition where a gate voltage is not applied, a current flows (an ON state). When a gate voltage is applied in this state, a depletion layer is generated on the periphery of the gate electrode 1204, and a current does not flow (an OFF state). With the aforementioned mechanism, the element operates as a transistor.

In a vertical transistor, a material which has both a carrier-transporting property and good film quality is required for an active layer, similarly to a light-emitting element. The acenaphthopyridine derivative according to the present invention sufficiently meets this requirement and is effective.

Embodiment 5

In this embodiment, an example of a light-emitting device manufactured using the light-emitting element described in Embodiment 2 or 3 will be described. Note that a light-emitting device according to the present invention is not limited to a light-emitting device having a structure to given below, and it includes all modes including the light-emitting element described in Embodiment 2 or 3 for a display portion (e.g., a pixel portion 602 in this embodiment).

Figure 3A:
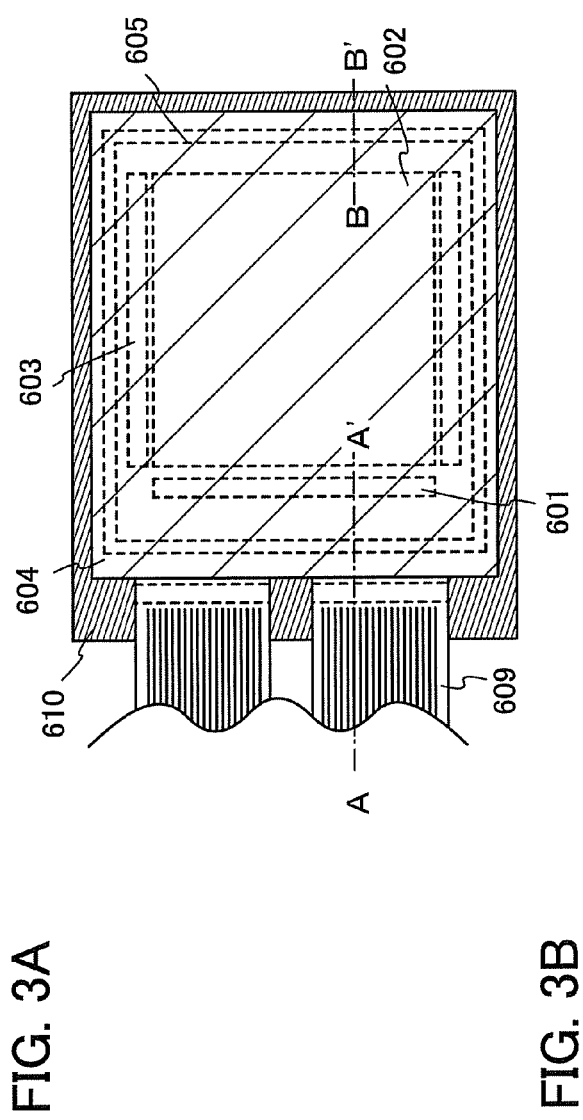
FIGS. 3A and 3B illustrate a light-emitting device according to an embodiment of the present invention.
Figure 3B:
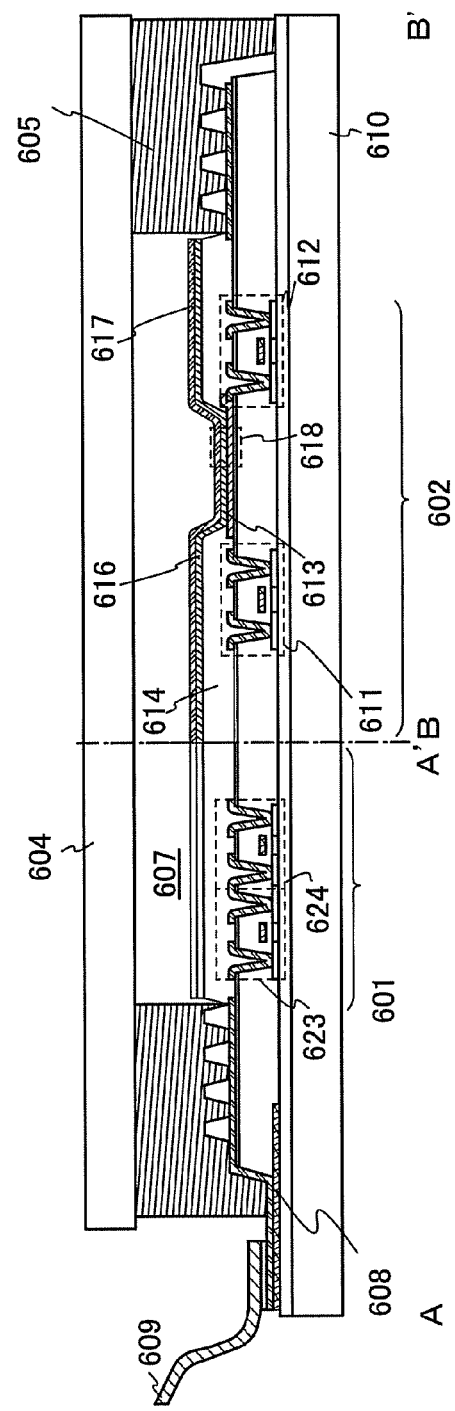

In this embodiment, an example of a light-emitting device manufactured using the light-emitting element described in Embodiment 2 or 3 will be described with reference to FIGS. 3A and 3B. Note that FIG. 3A is a top view of a light-emitting device and FIG. 3B is a cross-sectional view of FIG. 3A taken along lines A-A' and B-B'. This light-emitting device includes a driver circuit portion (source side driver circuit) 601, a pixel portion 602, and a driver circuit portion (gate side driver circuit) 603 each denoted by a dashed line, in order to control light emission of the light-emitting element. Further, reference numeral 604 indicates a sealing substrate and reference numeral 605 indicates a sealing material. A space 607 is provided inside of a portion surrounded by the sealing material 605.

A lead wiring 608 is a wiring for transmitting signals to be input to the source side driver circuit 601 and the gate side driver circuit 603. The lead wiring 608 receives video signals, clock signals, start signals, reset signals, and the like from an FPC (flexible printed circuit) 609 that serves as an external input terminal. Although only the FPC is illustrated here, the FPC may be provided with a printed wiring board (PWB). The light-emitting device in this specification includes not only a light-emitting device body but also a state in which an FPC or a PWB is attached to a light-emitting device.

Next, a cross-sectional structure will be described with reference to FIG. 3B. The driver circuit portions and the pixel portion are provided over an element substrate 610, but only the source side driver circuit 601, which is the driver circuit portion, and one pixel of the pixel portion 602 are illustrated.

A CMOS circuit with a combination of an n-channel TFT 623 and a p-channel TFT 624 is provided in the source side driver circuit 601. The driver circuit may be formed by using any of a variety of CMOS circuits, PMOS circuits, or NMOS circuits. It is not always necessary to form a driver-integrated type in which a driver circuit is formed over a substrate as in this embodiment, and it is also possible to form a driver circuit not over a substrate but outside the substrate.

The pixel portion 602 has a plurality of pixels, each of which includes a switching TFT 611, a current control TFT 612, a first electrode 613 electrically connected to a drain of the current control TFT 612, and a light-emitting element including the first electrode 613, a layer including an organic compound 616, and a second electrode 617. An insulator 614 is formed to cover the edge of the first electrode 613. Here, a positive photosensitive acrylic resin film is used to form the insulator 614.

In order to improve the coverage, the insulator 614 is provided such that either an upper edge portion or a lower edge portion thereof has a curved surface with a curvature. For example, in the case of using positive photosensitive acrylic for the insulator 614, only the upper edge portion of the insulator 614 preferably has a curved surface with a radius of curvature of 0.2 to 3 µm. Further, the insulator 614 can be formed using either negative photosensitive acrylic that becomes insoluble in an etchant due to light irradiation, or positive photosensitive acrylic that becomes dissoluble in an etchant due to light irradiation.

The layer 616 including an organic compound and the second electrode 617 are stacked over the first electrode 613, so that a light-emitting element is formed. As a material used for the first electrode 613 serving as an anode, a metal, an alloy, a conductive compound, a mixture thereof, or the like having a high work function (specifically, greater than or equal to 4.0 eV) is preferably used. Specifically, a single layer of indium tin oxide (hereinafter also referred to as ITO), indium tin oxide including silicon or silicon oxide, indium oxide including zinc oxide (ZnO), indium oxide including tungsten oxide and zinc oxide (IWZO), gold (Au), platinum (Pt), nickel (Ni), tungsten (W), chromium (Cr), molybdenum (Mo), iron (Fe), cobalt (Co), copper (Cu), palladium (Pd), or a nitride of the metal material (e.g., titanium nitride), can be used. Moreover, a layered structure can also be employed, and a layered structure of a film including titanium nitride as its main component and a film including aluminum as its main component, a three-layer structure including a titanium nitride film, a film including aluminum as its main component, and a titanium nitride film, or the like can be used. With the layered structure, low wiring resistance, favorable ohmic contact, and a function as the anode can be achieved. By using the composite layer as described in Embodiment 2 as a hole-injecting layer, a material of the first electrode can be selected regardless of its work function.

The layer 616 including an organic compound has a structure similar to that of the layer 103 including an organic compound described in Embodiment 2. Either a low-molecular compound or a high-molecular compound (including an oligomer and a dendrimer) may be employed as the material for forming the layer 616 including an organic compound. Moreover, not only an organic compound but also an inorganic compound can be used for the material of the layer 616 including an organic compound, partly. In addition, the layer 616 including an organic compound is formed by any of a variety of methods such as an evaporation method using an evaporation mask, an ink-jet method, and a spin coating method.

As a material of the second electrode 617 which is formed over the layer 616 including an organic compound and serves as a cathode, a material having a low work function (Al, Mg, Li, Ca, or an alloy or a compound thereof, such as MgAg, MgIn, AlLi, LiF, or $CaF_2$) is preferably used. In the case where light generated in the layer 616 including an organic compound is transmitted through the second electrode 617, stacked layers of a metal thin film with a reduced thickness and a transparent conductive film (ITO, indium oxide including 2 to 20 wt % zinc oxide, indium oxide-tin oxide including silicon or silicon oxide, zinc oxide (ZnO), or the like) are preferably used as the second electrode 617. By using an electron-injecting layer as described in Embodiment 2, a material of the second electrode can be selected regardless of its work function.

As described above, the light-emitting element includes the first electrode 613, the layer 616 including an organic compound, and the second electrode 617. The specific structures and materials of the light-emitting element have been described in Embodiment 2, and the repeated description is omitted. The description in Embodiment 2 is to be referred to. Note that the first electrode 613, the layer 616 including an organic compound, and the second electrode 617 in this embodiment correspond to the anode 100, the layer 103 including an organic compound, and the cathode 101 in Embodiment 1, respectively.

The element substrate 610 provided with the light-emitting element and the TFTs for the driver circuit and the pixel portion as described above is attached to the sealing substrate 604 with the sealing material 605, whereby a light-emitting device in which a light-emitting element 618 as described in Embodiment 2 is disposed in the space 607 surrounded by the element substrate 610, the sealing substrate 604, and the sealing material 605 can be formed. Further, the space 607 is filled with filler. The space is also filled with an inert gas (such as nitrogen or argon), and in some cases, the space is filled with the sealing material 605.

It is preferable that the sealing material 605 be an epoxy-based resin and a material of the sealing material 605 allow as little passage of oxygen as possible. In addition, as the sealing substrate 604, a plastic substrate formed of FRP (fiberglass-reinforced plastics), PVF (polyvinyl fluoride), polyester, acrylic, or the like can be used, in addition to a glass substrate or a quartz substrate.

In the above manner, a light-emitting device according to the present invention, which is manufactured using the light-emitting element described in Embodiment 2 or 3 can be obtained.

The light-emitting device of this embodiment includes the light-emitting element described in Embodiment 2 or 3, and the light-emitting element is an element whose drive voltage is reduced, so that a light-emitting device in which power consumption is reduced can be obtained.

Figure 4A:
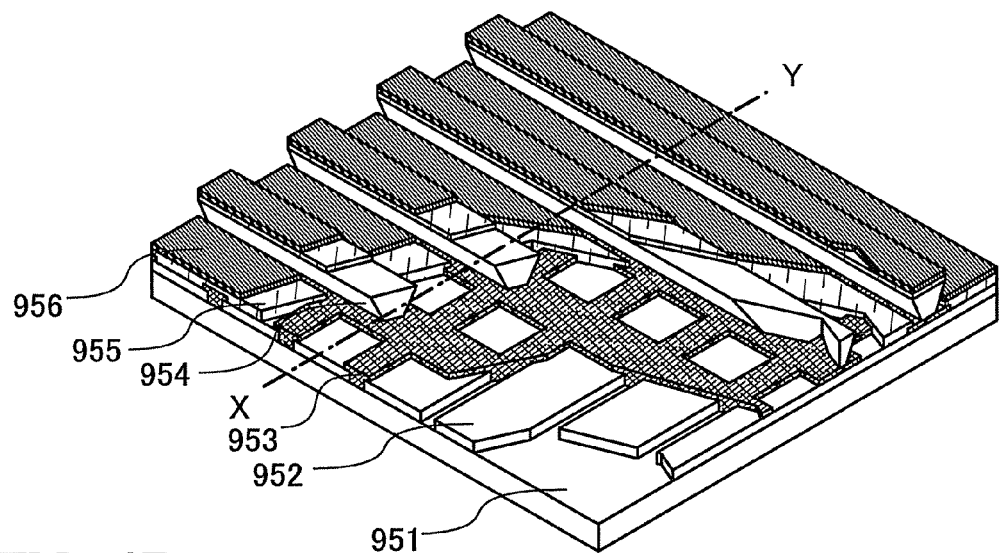
FIGS. 4A and 4B illustrate a light-emitting device according to an embodiment of the present invention.
Figure 4B:
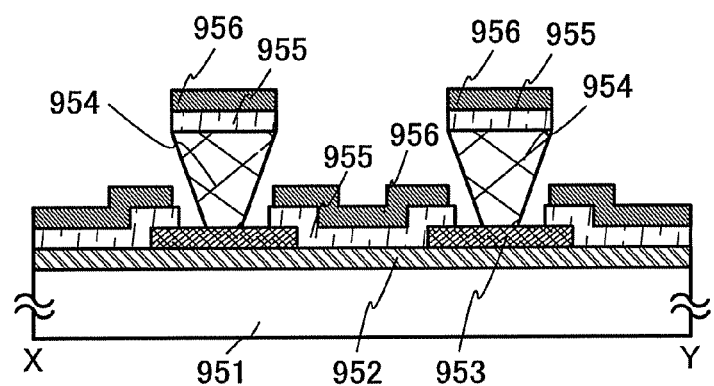

Although this embodiment describes an active matrix light-emitting device in which the driving of a light-emitting element is controlled by a transistor, the light-emitting device may also be a passive matrix light-emitting device. FIG. 4A is a perspective view of a passive matrix light-emitting device manufactured by applying the light-emitting element described in Embodiment 2 or 3. FIG. 4A is a perspective view of the light-emitting device and FIG. 4B is a cross-sectional view taken along line X-Y of FIG. 4A. In FIGS. 4A and 4B, over a substrate 951, a layer 955 including an organic compound is provided between an electrode 952 and an electrode 956. The edge of the electrode 952 is covered with an insulating layer 953. A partition layer 954 is provided over the insulating layer 953. The sidewalls of the partition layer 954 are aslope such that a distance between both sidewalls is gradually smaller toward the surface of the substrate. In other words, a cross section taken in the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other one of the pair of parallel sides). By providing the partition layer 954 in this manner, defects of the light-emitting element due to static electricity and the like can be prevented. The passive matrix light-emitting device can also be manufactured by including the light-emitting element described in Embodiment 2 or 3. Since the light-emitting device is manufactured by using the light-emitting element whose drive voltage is reduced, power consumption of the light-emitting device can be reduced.

Embodiment 6

In this embodiment, electronic appliances each including, as a part thereof, the light-emitting device described in Embodiment 5 will be described. These electronic appliances each have a display portion including the light-emitting element described in Embodiment 2 or 3.

Examples of the electronic appliance including the light-emitting element, which is described in Embodiment 2 or 3 and includes the acenaphthopyridine derivative described in Embodiment 1, include: cameras such as video cameras and digital cameras, goggle-type displays, navigation systems, audio reproducing devices (such as car audio components and audio components), computers, game machines, portable information terminals (such as mobile computers, mobile phones, mobile game machines, and electronic book readers), and image reproducing devices provided with a recording medium (specifically, a device which reproduces a recording medium such as a digital versatile disc (DVD) and has a display device for displaying the image). Such electronic appliances are specifically illustrated in FIGS. 5A to 5D.

Figure 5A:
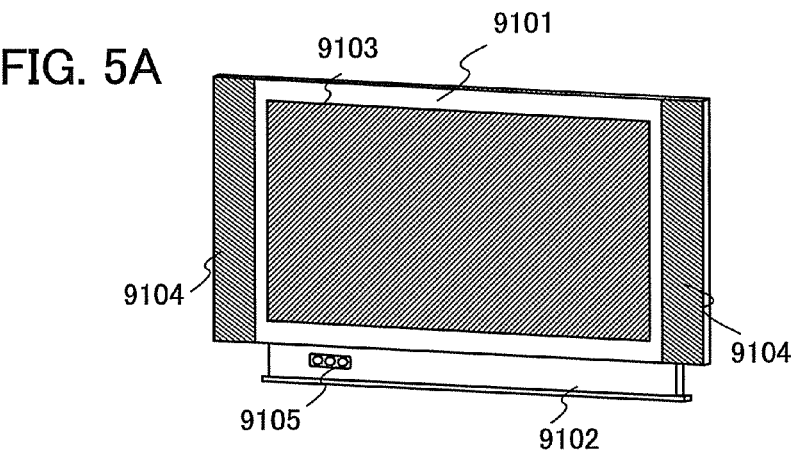
FIGS. 5A to 5D each illustrate an electronic appliance according to an embodiment of the present invention.

FIG. 5A illustrates a television device, which includes a chassis 9101, a support 9102, a display portion 9103, speaker portions 9104, a video input terminal 9105, and the like. In this television device, the display portion 9103 is manufactured with the use of the light-emitting element described in Embodiment 2 or 3 as a display element. Since the television device is manufactured using the light-emitting element whose drive voltage is reduced, power consumption of the display portion 9103 can be reduced. Thus, the television device provided with the display portion 9103 can be a television device in which power consumption is reduced.

Figure 5B:
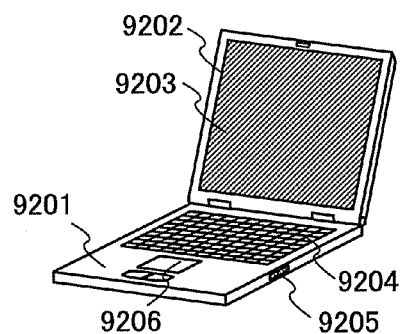

FIG. 5B illustrates a computer, which includes a main body 9201, a chassis 9202, a display portion 9203, a keyboard 9204, an external connection port 9205, a pointing device 9206, and the like. In this computer, the display portion 9203 is manufactured with the use of the light-emitting element described in Embodiment 2 or 3 as a display element. Since the display portion 9203 is manufactured using the light-emitting element whose drive voltage is reduced, power consumption thereof can be reduced. Thus, the computer provided with the display portion 9203 can be a computer in which power consumption is reduced.

Figure 5C:
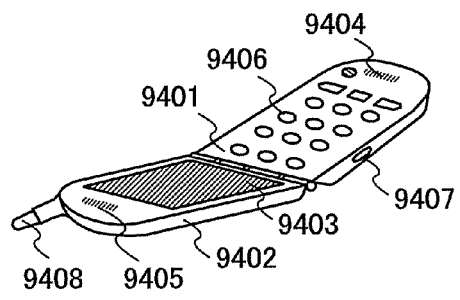

FIG. 5C illustrates a mobile phone, which includes a main body 9401, a chassis 9402, a display portion 9403, an audio input portion 9404, an audio output portion 9405, operation keys 9406, an external connection port 9407, an antenna 9408, and the like. In this mobile phone, the display portion 9403 is manufactured with the use of the light-emitting element described in Embodiment 2 or 3 as a display element. Since the display portion 9403 is manufactured using the light-emitting element whose drive voltage is reduced, power consumption thereof can be reduced. Thus, the mobile phone provided with the display portion 9403 can be a mobile phone in which power consumption is reduced. Low power consumption is a very advantageous point for mobile phones which are to be carried.

Figure 5D:
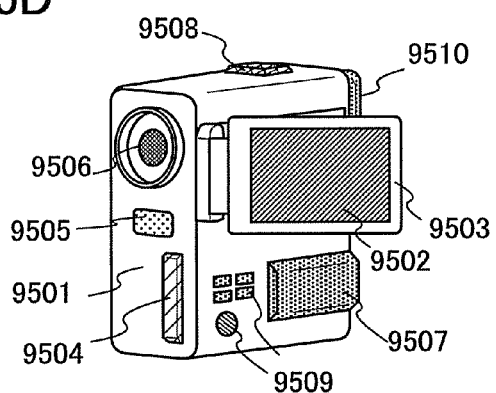

FIG. 5D illustrates a camera, which includes a main body 9501, a display portion 9502, a chassis 9503, an external connection port 9504, a remote control receiving portion 9505, an image receiving portion 9506, a battery 9507, an audio input portion 9508, operation keys 9509, an eyepiece portion 9510, and the like. In this camera, the display portion 9502 is manufactured with the use of the light-emitting element described in Embodiment 2 or 3 as a display element. Since the display portion 9502 is manufactured using the light-emitting element whose drive voltage is reduced, power consumption thereof can be reduced. Thus, the camera provided with the display portion 9502 can be a camera in which power consumption is reduced. Low power consumption is a very advantageous point for cameras which are often carried.

As described above, the application range of the light-emitting device manufactured using the light-emitting element described in Embodiment 2 or 3 is so wide that the light-emitting device can be applied to electronic appliances of various fields.

In addition, a light-emitting device according to the present invention can also be used for a lighting device. An embodiment in which the light-emitting element described in Embodiment 2 or 3 is applied to a lighting device will be described with reference to FIG. 6.

Figure 6:
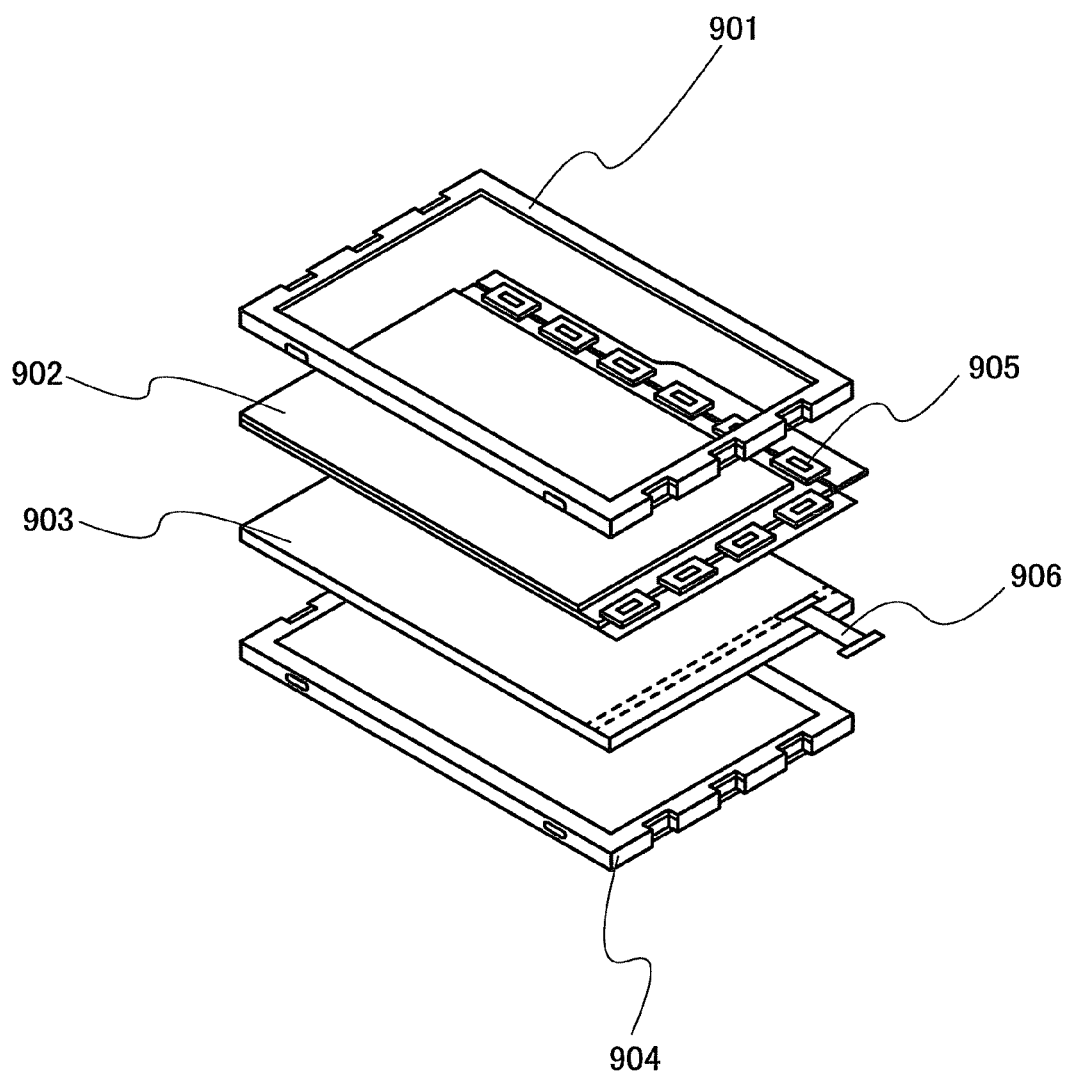
FIG. 6 illustrates an electronic appliance according to an embodiment of the present invention.

FIG. 6 illustrates an example of a liquid crystal display device in which the light-emitting element described in Embodiment 2 or 3 is employed as a backlight. The liquid crystal display device illustrated in FIG. 6 includes a chassis 901, a liquid crystal layer 902, a backlight unit 903, and a chassis 904. The liquid crystal layer 902 is connected to a driver IC 905. In addition, the backlight unit 903 is formed using the light-emitting element described in Embodiment 2 or 3, and a current is supplied thereto via a terminal 906.

Note that only one light-emitting element or a plurality of the light-emitting elements, described in Embodiment 2 or 3, may be used for the backlight unit 903.

In this manner, the light-emitting element which is described in Embodiment 2 or 3 and includes the acenaphthopyridine derivative described in Embodiment 1 can be applied to the backlight of the liquid crystal display device. Since the area of the backlight can be enlarged, the area of the liquid crystal display device can also be enlarged. The backlight formed using the light-emitting element which is described in Embodiment 2 or 3 and includes the acenaphthopyridine derivative described in Embodiment 1 can be a backlight in which low power consumption is achieved. Further, since the backlight does not need a thick component, the total thickness of the liquid crystal display device can be reduced.

Figure 7:
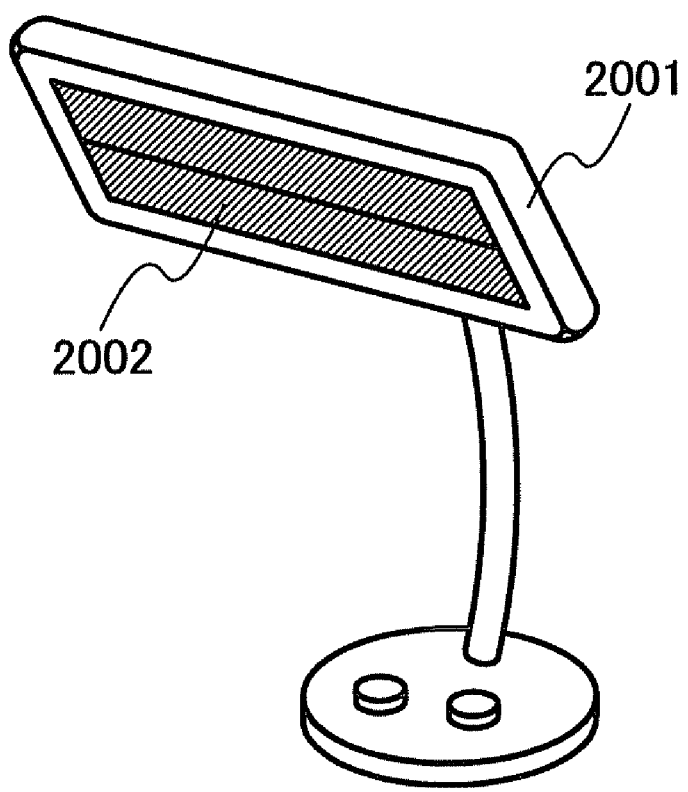
FIG. 7 illustrates a lighting device according to an embodiment of the present invention.

FIG. 7 illustrates an example in which the light-emitting element which is described in Embodiment 2 or 3 and includes the acenaphthopyridine derivative described in Embodiment 1 is used for a table lamp which is a lighting device. The table lamp illustrated in FIG. 7 includes a chassis 2001 and a light source 2002, and the light-emitting element which is described in Embodiment 2 or 3 and includes the acenaphthopyridine derivative described in Embodiment 1 is used for the light source 2002. The light source 2002 may be formed using one light-emitting element or a plurality of the light-emitting elements, described above. In addition, the light-emitting element which is described in Embodiment 2 or 3 and includes the acenaphthopyridine derivative described in Embodiment 1 may be combined with other light-emitting elements. Further, plural types of light-emitting elements which emit different colors from each other may be used. In this manner, the light source 2002 can be manufactured using the light-emitting element which is described in Embodiment 2 or 3 and includes the acenaphthopyridine derivative described in Embodiment 1. The table lamp manufactured using the light-emitting element whose drive voltage is reduced can be a table lamp in which low power consumption is achieved.

Figure 8:
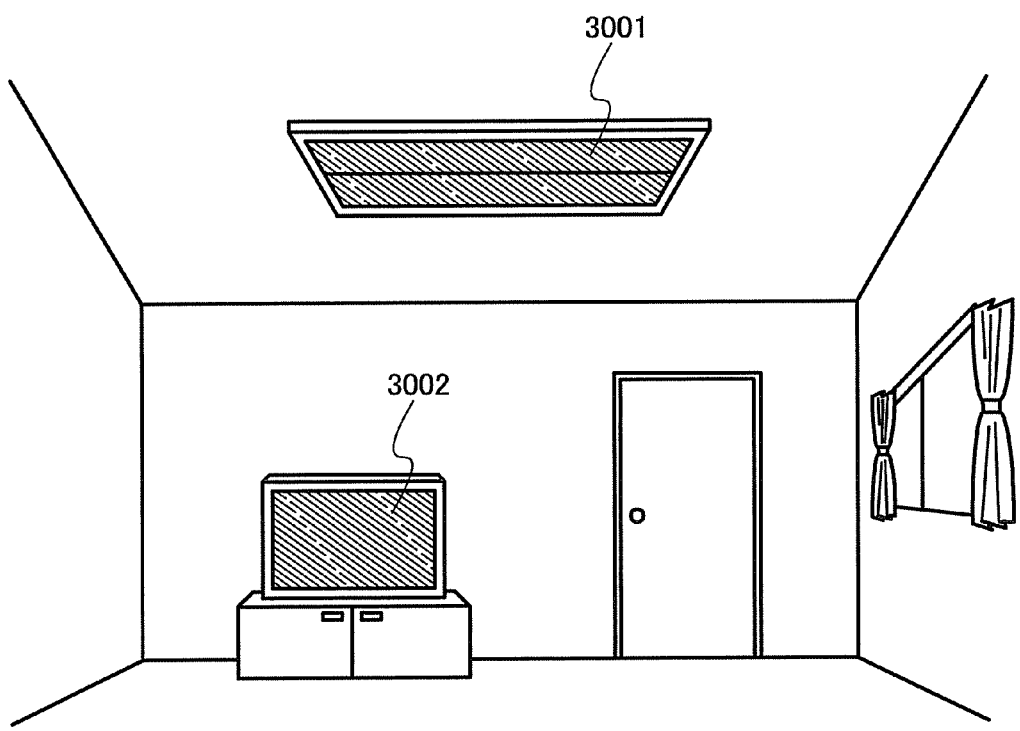
FIG. 8 illustrates a lighting device according to an embodiment of the present invention.

FIG. 8 illustrates an example in which the light-emitting element which is described in Embodiment 2 or 3 and includes the acenaphthopyridine derivative described in Embodiment 1 is used for an interior lighting device 3001. The lighting device 3001 may be formed using one light-emitting element or a plurality of the light-emitting elements, described above. In addition, the light-emitting element which is described in Embodiment 2 or 3 and includes the acenaphthopyridine derivative described in Embodiment 1 may be combined with other light-emitting elements. Further, plural types of light-emitting elements which emit different colors from each other may be used. In this manner, the lighting device 3001 can be manufactured using the light-emitting element which is described in Embodiment 2 or 3 and includes the acenaphthopyridine derivative described in Embodiment 1. The area of the lighting device 3001 formed using the light-emitting element can be enlarged, and thus, it can be used as a large-area lighting device. The lighting device 3001 manufactured using the light-emitting element whose drive voltage is reduced can be a lighting device in which low power consumption is achieved. Also, the light-emitting element which is described in Embodiment 2 or 3 and includes the acenaphthopyridine derivative described in Embodiment 1 is used for a television device 3002 according to the present invention, which is placed so that public broadcasting and movies can be watched.

Example 1

In this example, a synthesis method of 8-(2-pyridyl)-acenaphtho[1,2-b]pyridine (AQPy) which is represented by the structural formula (1) in Embodiment 1 will be described.

Step 1: Synthesis of Pyridine-2-carboxyamidrazone 2-cyanopyridine of 21 g (0.20 mol), ethanol of 200 mL, and hydrazine monohydrate of 33 mL (0.68 mol) were put in a 500-mL three-neck flask. This solution was stirred at room temperature for two days under a nitrogen stream. After a predetermined time, water was added to the solution, and an aqueous layer was extracted with chloroform. The obtained extract was washed with a saturated saline solution and then dried with magnesium sulfate. This mixture was subjected to gravity filtration, and the filtrate was condensed to obtain a solid. Hexane is added to the obtained solid and the suspension was irradiated with ultrasonic waves and subjected to suction filtration, so that white powder of 20 g, which was a target of this synthesis, was obtained at a yield of 76%. The synthesis scheme of Step 1 is shown in (a-1).

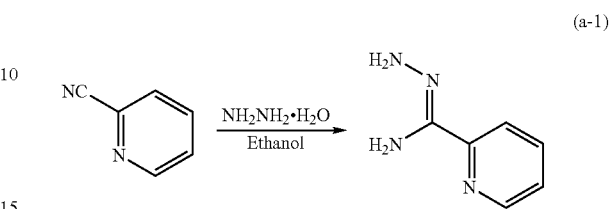

(a-1)

Step 2: Synthesis of 9-(2-pyridyl)-7,8,10-triaza-fluoranthene

Pyridine-2-carboxyamidrazone of 3.0 g (22 mmol) which was synthesized in Step 1, acenaphthene-1,2-dione of 4.4 g (24 mmol), and ethanol of 100 mL were put in a 300-mL three-neck flask. This solution was refluxed for 7 hours. After the reflux, the mixture was cooled to room temperature and then subjected to filtration, so that a solid was removed. The obtained filtrate was extracted with chloroform, and the extract was washed with water, together with an organic layer. After that, the organic layer was dried with magnesium sulfate. This mixture was filtered and a compound obtained by condensing the filtrate was recrystallized with chloroform, so that a target of 0.84 g was obtained at a yield of 14%. The synthesis scheme of Step 2 is shown in (a-2).

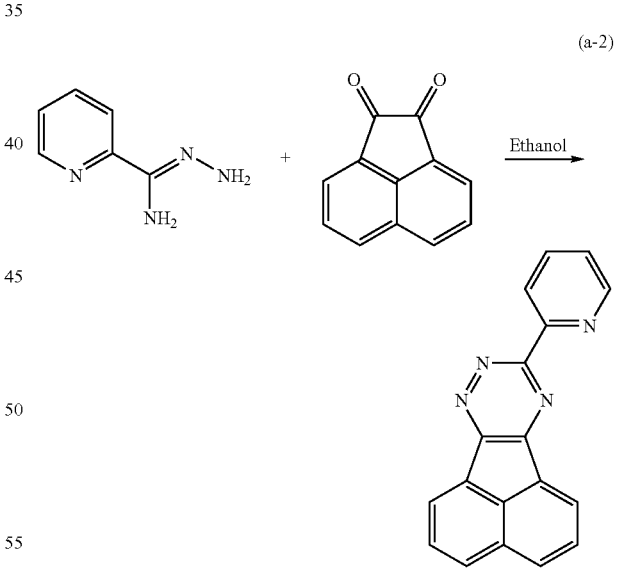

(a-2)

Step 3: Synthesis of 8-(2-pyridyl)-acenaphtho[1,2-b]pyridine 9-(2-pyridyl)-7,8,10-triaza-fluoranthene of 2.9 g (10 mmol) which was synthesized in Step 2 and 1,2-dichlorobenzene of 120 mL were put in a 300-mL three-neck flask. Bicyclo[2,2,1]hepta-2,5-diene of 5.9 mL (58 mmol) was added to this solution and the obtained solution was refluxed at 145° C. for 3 hours. After the reflux, the solution was condensed and a solvent was removed, so that a target compound was obtained. The obtained compound was purified by sublimation using train sublimation. The purification by sublimation was performed by heating the material at 200° C. at a reduced pressure under an argon stream. After the purification by sublimation, a target yellow solid was obtained. The synthesis scheme of Step 3 is shown in (a-3).

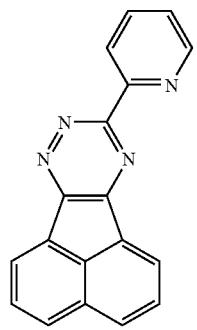

(a-3)

bicycro[2,2,1]hepta-2,5-diene
1,2-dichlorobenzene
→

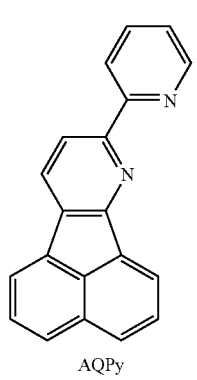

AQPy $^1$H NMR of the obtained yellow solid was measured, whereby it was confirmed that the yellow solid was 8-(2-pyridyl)-acenaphtho[1,2-b]pyridine (AQPy) which was represented by the structural formula (1) in Embodiment 1. The measurement result is described below.

$^1$H NMR (CDCl$_3$, 300 MHz): δ=7.33-7.36 (m, 1H), 7.68-7.81 (m, 2H), 7.89 (dt, J1=2.1 Hz, J2=7.5 Hz, 1H), 7.95-8.04 (m, 3H), 8.29 (d, J=8.4 Hz, 1H), 8.39 (d, J=6.5 Hz, 1H), 8.45 (d, J=7.5 Hz, 1H), 8.69 (d, J=8.4 Hz, 1H), 8.73 (d, J=5.1 Hz, 1H).

Figure 9A:
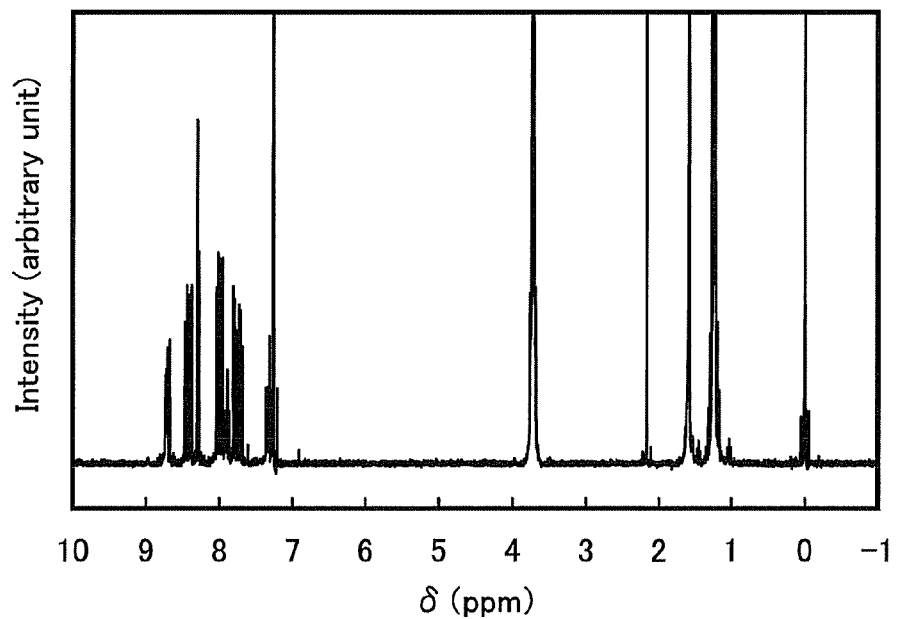
FIGS. 9A and 9B are $^1$H NMR charts of AQPy.
Figure 9B:
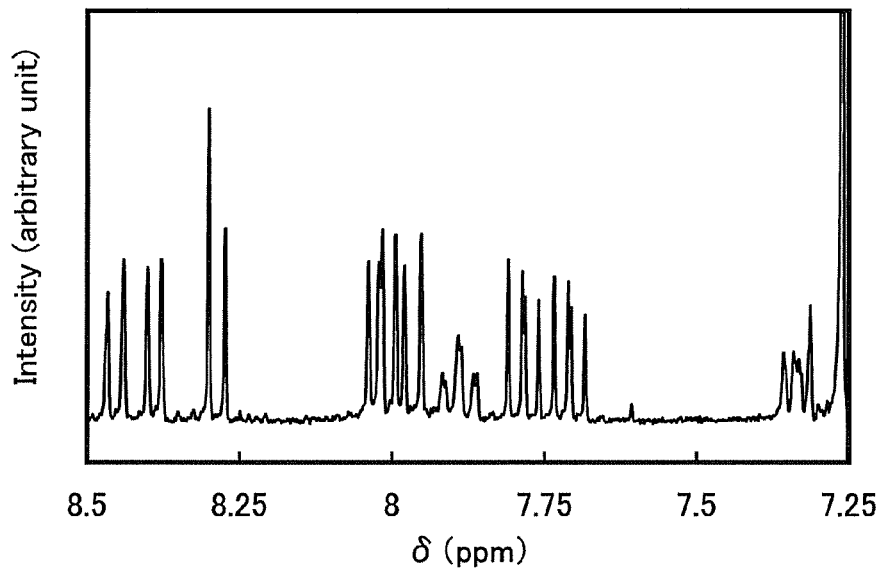
Figure 10:
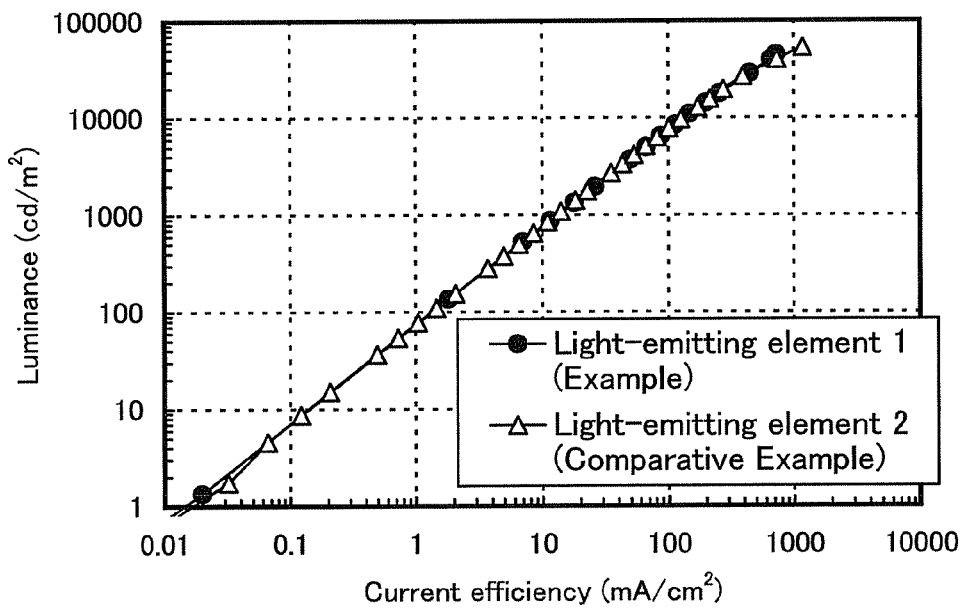
FIG. 10 is a graph showing current density vs. luminance characteristics of a light-emitting element 1 and a light-emitting element 2.
Figure 11:
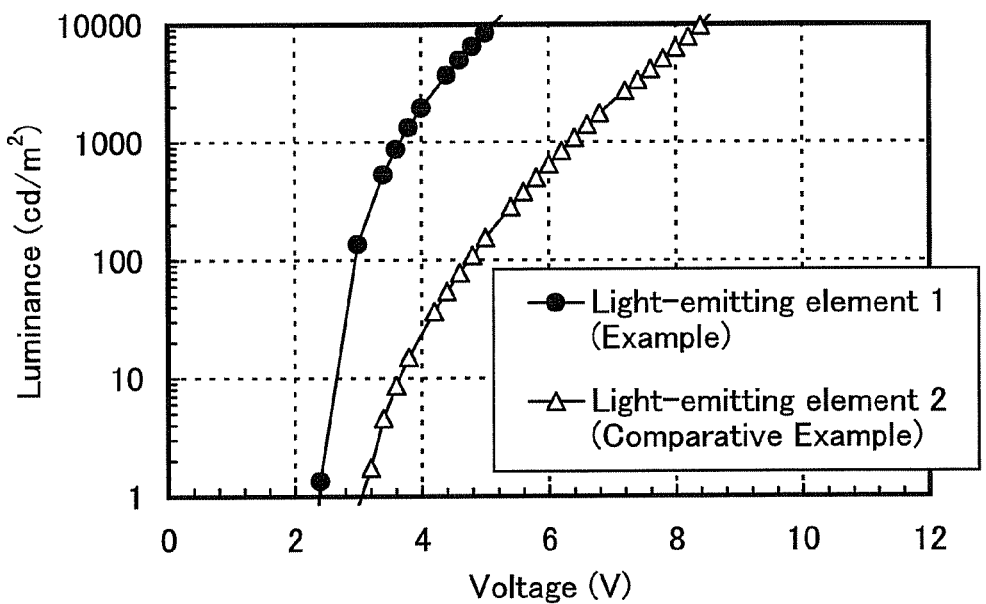
FIG. 11 is a graph showing voltage vs. luminance characteristics of a light-emitting element 1 and a light-emitting element 2.
Figure 12:
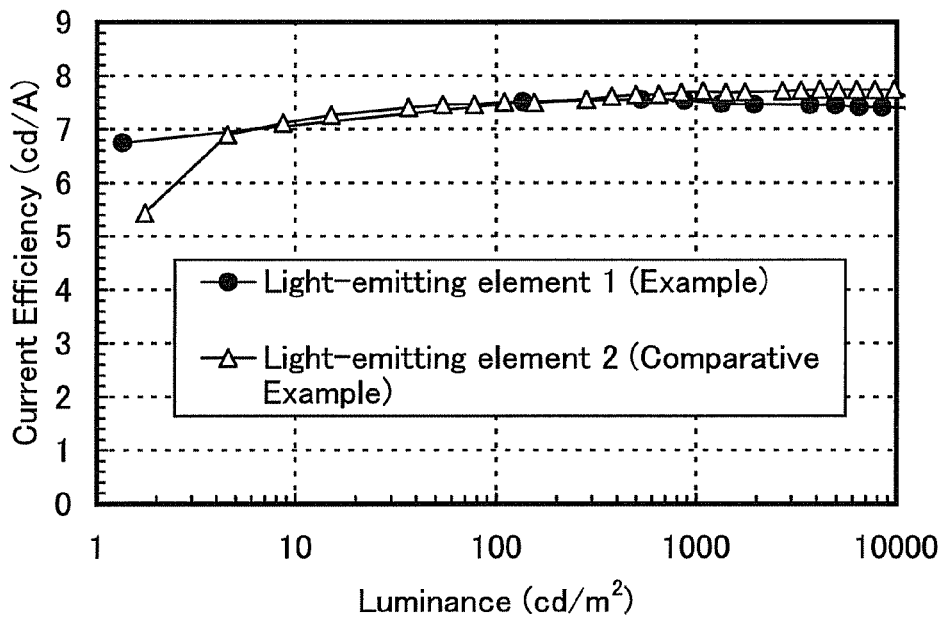
FIG. 12 is a graph showing luminance vs. current efficiency characteristics of a light-emitting element 1 and a light-emitting element 2.
Figure 13:
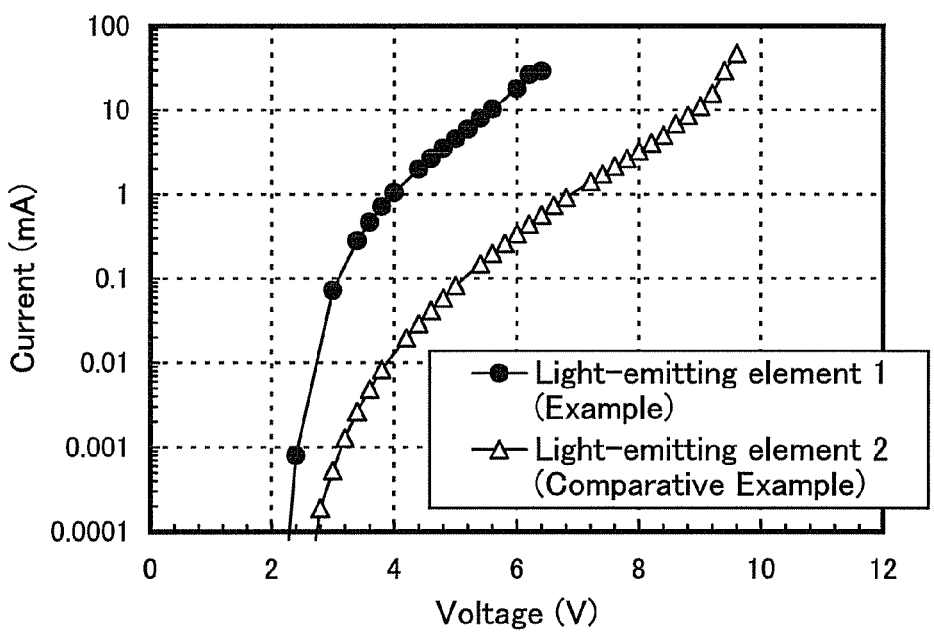
FIG. 13 is a graph showing voltage vs. current characteristics of a light-emitting element 1 and a light-emitting element 2.

FIGS. 9A and 9B are $^1$H NMR charts. FIG. 9B is a chart in which the range of 7.25 to 8.5 ppm in FIG. 9A is enlarged.

As described above, 8-(2-pyridyl)-acenaphtho[1,2-b]pyridine which is represented by the structural formula (1) in Embodiment 1 can be synthesized according to this example.

Example 2

In this example, a light-emitting element in which the acenaphthopyridine derivative described in Embodiment 1 is used for an electron-transporting layer will be described.

The molecular structures of organic compounds used in this example are represented by the following structural formulas (i) to (iv). An element structure is the same as that of FIG. 1A.

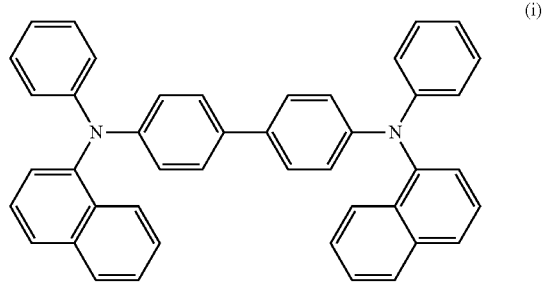

NPB

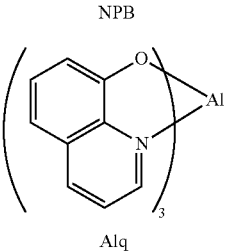

Alq

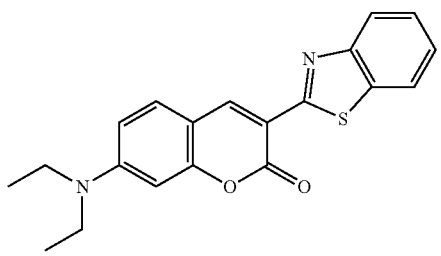

coumarin 6

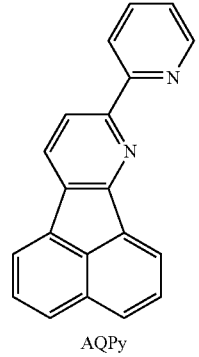

AQPy

Manufacturing of Light-Emitting Element 1
(Example)

First, a glass substrate over which a film of indium tin oxide including silicon (ITSO) with a thickness of 110 nm had been formed as an anode 100 was prepared. The periphery of the surface of the ITSO film was covered with a polyimide film so that an area of 2 mm×2 mm of the surface was exposed, so that the electrode area was 2 mm×2 mm. As pretreatment for forming a light-emitting element over the substrate, the surface of the substrate was washed with water, and baked at 200° C. for one hour, and then, UV ozone treatment was conducted for 370 seconds. Then, the substrate was carried into a vacuum evaporation apparatus in which the pressure was reduced to about 10$^{-4}$ Pa, and vacuum baking at 170° C. for 30 minutes was conducted in a heating chamber of the vacuum evaporation apparatus, and then, the substrate was cooled down for about 30 minutes.

Then, the substrate was fixed on a holder provided in the vacuum evaporation apparatus such that the surface of the substrate provided with the ITSO film faced down.

After the pressure in the vacuum evaporation apparatus was reduced to $10^{-4}$ Pa, 4,4'-bis[N-(1-naphthyl)-N-phenylamino]biphenyl (NPB) represented by the above structural formula (i) and molybdenum(VI) oxide were co-evaporated so as to meet NPB:molybdenum(VI) oxide=4:1 (mass ratio), whereby a hole-injecting layer 104 was formed. The thickness of the hole-injecting layer 104 was 50 nm. Note that the co-evaporation is an evaporation method in which a plurality of substances different from each other are concurrently evaporated from evaporation sources different from each other. Next, NPB was evaporated to be 10 nm thick, whereby a hole-transporting layer 105 was formed.

Further, on the hole-injecting layer 105, tris(8-quinolinolato)aluminum(III) (Alq) represented by the above structural formula (ii) and coumarin 6 represented by the above structural formula (iii) were co-evaporated so as to meet Alq: coumarin 6=1:0.01 (mass ratio), whereby a light-emitting layer 102 was formed. The thickness of the light-emitting layer 102 was 40 nm.

Next, 8-(2-pyridyl)-acenaphtho[1,2-b]pyridine (AQPy) represented by the above structural formula (iv) was evaporated to be 30 nm thick, whereby an electron-transporting layer 106 was formed. Further, lithium fluoride was evaporated to be 1 nm thick on the electron-transporting layer 106, whereby an electron-injecting layer 107 was formed. Finally, a film of aluminum was formed to be 200 nm thick as a second electrode serving as a cathode 101, whereby a light-emitting element 1 was obtained. In the above evaporation process, each evaporation was performed by a resistance heating method.

Manufacturing of Light-Emitting Element 2
(Comparative Example)

A light-emitting element 2 was manufactured in a manner similar to that of the light-emitting element 1 except that the electron-transporting layer in the light-emitting element 1 was formed using Alq which was one of most popular electron-transporting materials.

Current density vs. luminance characteristics, voltage vs. luminance characteristics, luminance vs. current efficiency characteristics, and voltage vs. current characteristics of the light-emitting elements 1 and 2 are shown in FIG. 10, FIG. 11, FIG. 12, and FIG. 13, respectively. Table 1 shows values of these characteristics of the light-emitting elements 1 and 2 at 1000 cd/m².

|  | voltage (V) | Current (mA) | Current density (mA/cm²) | Current efficiency (cd/A) | Power efficiency (lm/W) |
| --- | --- | --- | --- | --- | --- |
| Light-emitting element 1 (Example) in using 874 cd/m² | 3.6 | 0.46 | 11.6 | 7.5 | 6.6 |
| Light-emitting element 2 (Comparative Example) in using 1080 cd/m² | 6.4 | 0.56 | 14.1 | 7.7 | 3.8 |

It is found that the light-emitting element in which AQPy that is the acenaphthopyridine derivative described in Embodiment 1 is used for the electron-transporting layer has about the same or substantially the same current efficiency but can be driven at a much lower voltage, compared to the light-emitting element in which Alq is used for the electron-transporting layer.

This application is based on Japanese Patent Application Serial No. 2008-086574 filed with Japan Patent Office on Mar. 28, 2008, the entire contents of which are hereby incorporated by reference.

The invention claimed is:

1. An acenaphthopyridine derivative represented by a following general formula (G1),

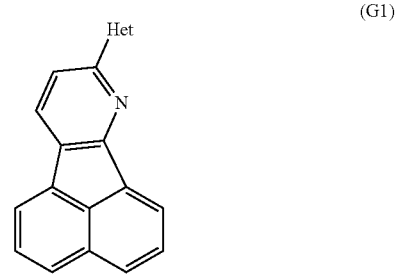

(G1)

wherein Het in the formula represents a pyridyl group or a quinolyl group.

2. An acenaphthopyridine derivative represented by a following general formula (G1), (G1)

wherein Het in the formula represents any one of substituents represented by following structural formulas (S1) to (S14):

(S1)

(S2)

(S3)

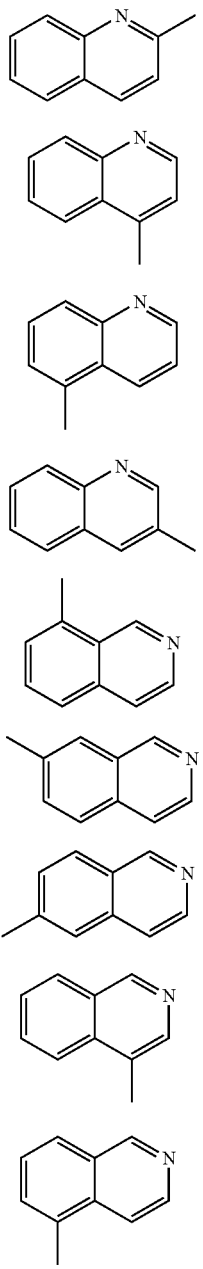

(S4)
(S5)
(S6)
(S7)
(S8)
(S9)
(S10)
(S11)
(S12)

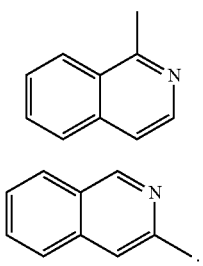

(S13)

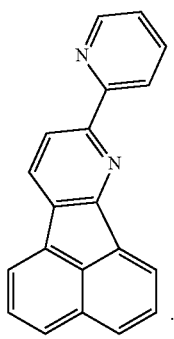

(S14)

3. An acenaphthopyridine derivative represented by a following general formula (1):

(1)

[structure of formula (1)]

4. A material of a light-emitting element, comprising the acenaphthopyridine derivative according to any one of claims 1 to 3.

5. A light-emitting element comprising the acenaphthopyridine derivative according to any one of claims 1 to 3.

6. A light-emitting element comprising the acenaphthopyridine derivative according to any one of claims 1 to 3 in an electron-transporting layer.

7. A light-emitting device comprising the light-emitting element according to claim 5 and a unit configured to control the light-emitting element.

8. A light-emitting device comprising the light-emitting element according to claim 6 and a unit configured to control the light-emitting element.

9. An electronic appliance comprising the light-emitting device according to claim 7.

10. An electronic appliance comprising the light-emitting device according to claim 8.

* * * * *